US012132419B2

(12) United States Patent
Corrigan et al.

(10) Patent No.: US 12,132,419 B2
(45) Date of Patent: Oct. 29, 2024

(54) LOW VOLTAGE ELECTROSTATIC JAMMING DEVICE

(71) Applicant: 3M INNOVATIVE PROPERTIES COMPANY, St. Paul, MN (US)

(72) Inventors: Thomas R. Corrigan, St. Paul, MN (US); David J. Rowe, Roseville, MN (US); Andrew H. Tilstra, Shoreview, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 127 days.

(21) Appl. No.: 17/932,471

(22) Filed: Sep. 15, 2022

(65) Prior Publication Data

US 2023/0017223 A1    Jan. 19, 2023

Related U.S. Application Data

(62) Division of application No. 17/252,500, filed as application No. PCT/IB2019/055421 on Jun. 26, 2019, now abandoned.
(Continued)

(51) Int. Cl.
*H02N 1/00* (2006.01)
*H02N 13/00* (2006.01)

(52) U.S. Cl.
CPC ............. *H02N 1/006* (2013.01); *H02N 13/00* (2013.01)

(58) Field of Classification Search
CPC ........... H02N 1/00; H02N 13/00; G06F 3/016
See application file for complete search history.

(56) References Cited

U.S. PATENT DOCUMENTS 2,897,934 A    8/1959   Fitch
7,598,652 B2  10/2009  Kornbluh
(Continued)

FOREIGN PATENT DOCUMENTS

WO    WO 2015-094375    6/2015

OTHER PUBLICATIONS

T. Wang et al. "Electrostatic Layer Jamming Variable Stiffness for Soft Robotics," in IEEE/ASME Transactions on Mechatronics, vol. 24, No. 2, pp. 424-433, Apr. 2019, doi: 10.1109/TMECH.2019.2893480. (Year: 2019).*
(Continued)

*Primary Examiner* — Burton S Mullins
(74) *Attorney, Agent, or Firm* — Sriram Srinivasan; X. Christina Huang

(57) ABSTRACT

At least some embodiments of the present disclosure an electrostatic sheet jamming device comprising a first sheet having a first conductive layer, a first dielectric layer disposed adjacent to the first conductive layer, and a second sheet comprising a second conductive layer and disposed proximate to the first dielectric layer. The first dielectric layer is disposed between the first conductive layer and the second conductive layer. The first sheet and the second sheet are non-extensible and flexible, wherein the first sheet and the second sheet are slidable relative to each other in a first state. The first sheet and the second sheet are jammed with each other in a second state when a voltage is applied between the first conductive layer and the second conductive layer. In some embodiments, the applied voltage is less than or equal to a break-down voltage of air at a distance between the first conductive layer and the second conductive layer.

15 Claims, 18 Drawing Sheets

Related U.S. Application Data

(60) Provisional application No. 62/691,446, filed on Jun. 28, 2018.

(56) References Cited

U.S. PATENT DOCUMENTS

| | | | |
|---|---|---|---|
| 8,515,510 | B2 | 8/2013 | MacLaughlin |
| 9,130,485 | B2 | 9/2015 | Prahlad |
| 9,401,668 | B2 | 7/2016 | Prahlad |
| 10,355,624 | B2 | 7/2019 | Majidi |
| 2014/0375170 | A1* | 12/2014 | Jenninger ............ H10N 30/857 310/311 |
| 2015/0343647 | A1 | 12/2015 | Garcia |
| 2017/0131769 | A1 | 5/2017 | Keller |
| 2017/0222576 | A1 | 8/2017 | Majidi |
| 2018/0143687 | A1 | 5/2018 | Moessinger |
| 2019/0339773 | A1 | 11/2019 | Holbery |
| 2020/0081532 | A1* | 3/2020 | Yoon ..................... G06F 3/0383 |
| 2020/0356168 | A1* | 11/2020 | Remaley ................ G06F 3/016 |

OTHER PUBLICATIONS

Babrauskas, "Arc Breakdown in Air over Very Small Gap Distances", Interflam, 2013, vol. 2, pp. 1489-1498.

Diller, "A Lightweight, Low-Power Electroadhesive Clutch and Spring for Exoskeleton Actuation", IEEE International Conference on Robotics and Automation (ICRA), 2016, pp. 682-689.

R.Hinchet et al. "DextrES: Wearable Haptic Feedback for Grasping in VR via a Thin Form-Factor Electrostatic Brake" Proceedings of the 31st Annual ACM Symposium on User Interface Software and Technology, Oct. 2018, pp. 901-912; https://doi.org/10.1145/3242587.3242657 (Year: 2018).

Imamura, "Dielectric Elastomer Actuator with Variable Stiffness based on Interlaminar Electrostatic Chucking", Proceedings of SPIE, 2017, vol. 10163, pp. 101630Q1-6, XP 060090199A.

International Search Report for PCT Application No. PCT/IB2019/055421, mailed on Dec. 12, 2019, 5 pages.

W. H. Choi, S. Kim, D. Lee and D. Shin, "Soft, Multi-DoF, Variable Stiffness Mechanism Using Layer Jamming for Wearable Robots," in IEEE Robotics and Automation Letters, vol. 4, No. 3, pp. 2539-2546, Jul. 2019, doi: 10.1109/LRA.2019.2908493. (Year: 2019).

I. Choi, N. Corson, L. Peiros, E.W. Hawkes, S. Keller and S. Follmer, "A Soft, Controllable, High Force Density Linear Brake, V Utilizing Layer Jamming," in IEEE Robotics and Automation Letters, vol. 3, No. 1, pp. 450-457, Jan. 2018, doi: 10.1109/LRA 2017.2761938. (Year: 2018).

Y.-J. Kim, S. Cheng, S. Kim and K. Iagnemma, "A Novel Layer Jamming Mechanism With Tunable Stiffness Capability for Minimally Invasive Surgery," in IEEE Transactions on Robotics, vol. 29, No. 4, pp. 1031-1042, Aug. 2013, doi: 10.1109/TRO .2013. 2256313. (Year: 2013).

J. Ou, L. Yao, D. Tauber, J. Steimle, R. Niiyama, and H. Ishii, "JamSheets:Thin interfaces with tunable stiffness enabled by layer jamming," in Proc. 8th Int. Conf. Tangible, Embedded Embodied Interact. ACM, 2014, pp. 65-72. (Year: 2014).

\* cited by examiner

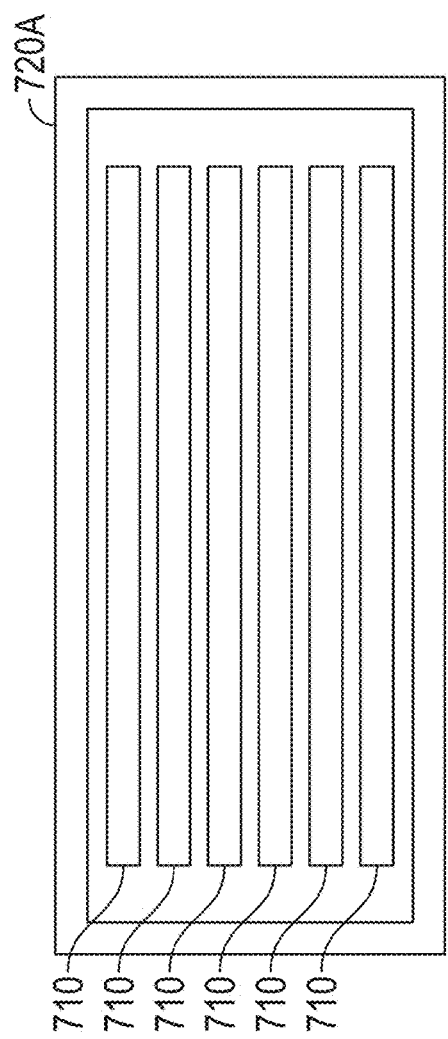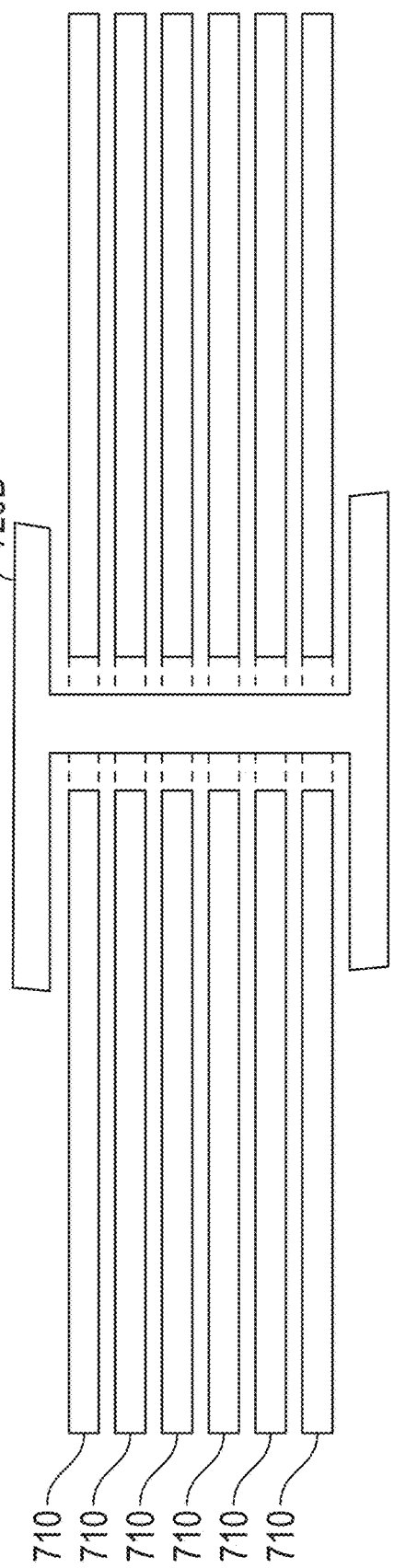

LOW VOLTAGE ELECTROSTATIC JAMMING DEVICE

CROSS REFERENCE TO RELATED APPLICATIONS

This application is a divisional of U.S. application Ser. No. 17/252,500, filed Dec. 15, 2020, which is a US 371 Application based on PCT/IB2019/055421, filed on Jun. 26, 2019, which claims the benefit of U.S. Provisional Application No. 62/691,446, filed Jun. 28, 2018, the disclosures of which are incorporated by reference in their entirety herein.

TECHNICAL FIELD

The present disclosure is related to jamming devices that can be used for motion resistance.

SUMMARY

At least some embodiments of the present disclosure direct to an electrostatic sheet jamming device comprising a first sheet having a first conductive layer, a first dielectric layer disposed adjacent to the first conductive layer, a second sheet comprising a second conductive layer and disposed proximate to the first dielectric layer. The first dielectric layer is disposed between the first conductive layer and the second conductive layer. The first dielectric layer has a thickness less than or equal to 10 micrometers. The first sheet and the second sheet are non-extensible and flexible, wherein the first sheet and the second sheet are slidable relative to each other in a first state. The first sheet and the second sheet are jammed with each other in a second state when a voltage is applied between the first conductive layer and the second conductive layer. The applied voltage is less than or equal to a break-down voltage of air at a distance between the first conductive layer and the second conductive layer.

At least some embodiments of the present disclosure direct to an electrostatic sheet jamming device comprising a first set of sheets, each of the first set of sheets comprising a first conductive layer, a second set of sheets, each of the second set of sheets comprising a second conductive layer, a set of dielectric layers, a first connector electrically conductively connected to first conductive layers of at least part of the first set of sheets, and a second connector electrically conductively connected to second conductive layers of at least part of the second set of sheets. The first set of sheets and the second set of sheets are interdigitated. Each of the adjacent pair of the first set of sheets and the second set of sheets has one of the set of dielectric layers disposed in between. Each of the set of dielectric layers has a thickness less than or equal to 10 micrometers. The first set of sheets and the second set of sheets are slidable relative to each other in a first state. The first set of sheets and the second set of sheets are jammed with each other in a second state when a voltage is applied between the first connector and the second connector. The applied voltage is less than or equal to a break-down voltage of air at a distance between adjacent conductive layers of one of the first set of sheets and one of the second set of sheets.

BRIEF DESCRIPTION OF DRAWINGS

The accompanying drawings are incorporated in and constitute a part of this specification and, together with the description, explain the advantages and principles of the invention. In the drawings.

FIGS. 7A and 7B illustrate some examples of urging components; and

Figure 1A:
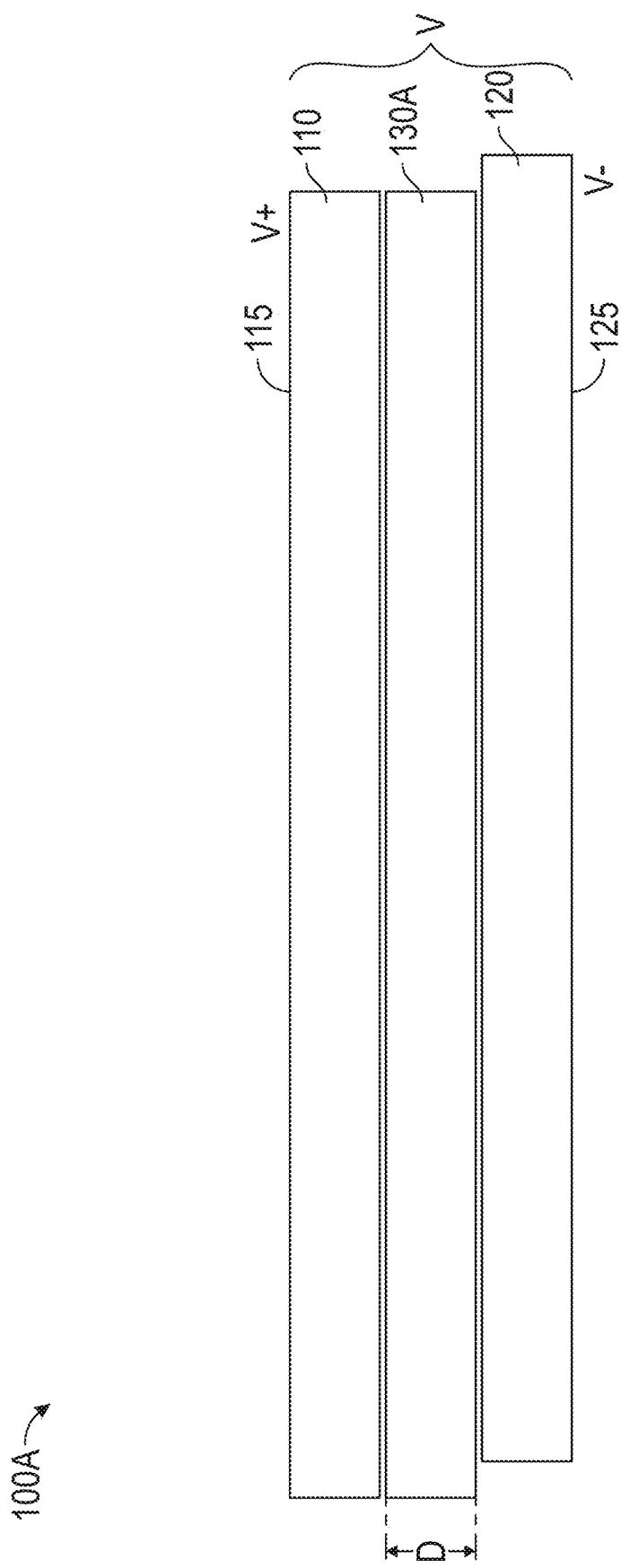
FIGS. 1A-1F illustrate several examples of electrostatic jamming devices.

In the drawings, like reference numerals indicate like elements. While the above-identified drawings, which may not be drawn to scale, set forth various embodiments of the present disclosure, other embodiments are also contemplated, as noted in the Detailed Description. In all cases, this disclosure describes the presently disclosed disclosure by way of representation of exemplary embodiments and not by express limitations. It should be understood that numerous other modifications and embodiments can be devised by those skilled in the art, which fall within the scope and spirit of this disclosure.

DETAILED DESCRIPTION

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below or beneath other elements would then be above those other elements.

As used herein, when an element, component or layer for example is described as being "on" "connected to," "coupled to" or "in contact with" another element, component or layer, it can be directly on, directly connected to, directly coupled with, in direct contact with, or intervening elements, components or layers may be on, connected, coupled or in contact with the particular element, component or layer, for example. When an element, component or layer for example is referred to as being "directly on," "directly connected to," "directly coupled to," or "directly in contact with" another element, there are no intervening elements, components or layers for example.

Articles with adjustable stiffness and variable resistance to motion are often needed. For example, a flexible display is bendable and capable of sustaining a bent position. At least some embodiments of the present disclosure are directed to an electrostatic jamming device that generates a controlled resistance to motion. Such a jamming device can be incorporated into various devices, systems, and structures to resist different motions, for example, bending motions, translations, rotations, and the like. The motions can be largely planar, or along or within surfaces.

Sheets of materials can be jammed together with vacuum to resist motion. Sheets of materials can be jammed together with electrostatics. This eliminates the need for a vacuum source and gas impermeable envelope. Previous electrostatic jamming devices had several limitations. Some devices enable only simple bending of sheets which can only be shaped into developable surfaces (or a smooth surface with zero Gaussian curvature). The previous devices tend to be difficult to build and operate at high voltages.

At least some embodiments of the present disclosure direct to a jamming device that can be used to allow bending in one state and resist bending in another state. In some embodiments, the jamming device includes multiple sheets and the sheets can be electrostatically jammed to resist motions. Such jamming device includes conductive layers and dielectric layers disposed between adjacent conductive layers. At least some embodiments of the present disclosure are directed to electrostatic jamming devices that can operate at low voltages yet achieve useful levels of motion resistance. Low voltage refers to a voltage that is lower than the break down voltage of air for the minimal distance between any two oppositely charged conductive layers. Some of the existing jamming devices include dielectric layers that extend well beyond conductive layers to make the shortest path in air between two oppositely charged conductors much longer than the path through the dielectric layer. This makes such jamming devices more difficult to fabricate and susceptible to pin holes or cracks in the dielectric layers because they would create a distance between oppositely charged conductors that would allow breakdown of the air (shorting and arcing). Some embodiments of the jamming devices in the present disclosure are immune to shorting or arcing despite cracks, cuts, pin holes, and other defects in the dielectric layers. In some embodiments, the conductive layers are held at or beyond the thickness of the dielectric layer and the jamming device is operated below the breakdown voltage of air for that distance. In some embodiments, jamming sheets can be cut from a continuous roll of material with no special treatment to the edges of the sheets and used to assemble a jamming device. This enables a low cost high speed manufacturing method for electrostatic sheet jamming devices where a roll of sheet material is created and then easily converted into a desired shape and assembled into a device. In some cases, the low voltage jamming device has the advantage of storing much less energy in the device and being safer for use on and near the human body.

Breakdown voltage refers to the voltage that will cause air to break down and become conductive across a gap of a given distance between two conductors. This is also known as arcing or sparking across the gap. The breakdown voltage varies with pressure. The present disclosure generally refers to the breakdown voltage of air within the range of standard pressures experienced on earth. In the present disclosure, the breakdown voltage refers to the shortest distance through air (not through other dielectric materials) between any two conductors that are not intentionally connected electrically. In the present disclosure, the value of the breakdown voltage at a given distance and pressure has been well studied for years and is generally accepted to follow Pashen's Law at gaps above several micrometers but deviate from it at smaller gaps. The breakdown voltage can be determined using a simplified formula proposed by Babrauskas, Vytenis, *Arc Breakdown in Air over Very Small Gap Distances*, Interflam 2013, Volume 2, pp. 1489-1498, as provided in Equation (1) below:

$$V = \begin{cases} 178 + 2.48d + 58\sqrt{d}, & d \geq 7 \text{ μm} \\ 337, & 3.5 \text{ μm} \leq d < 7 \text{ μm}, \\ 97d, & d \geq 3.5 \text{ μm} \end{cases} \quad (1)$$

where V is the breakdown voltage in Volt, d is the distance between the two conductors. Breakdown strength, also referred to as dielectric strength, can be understood as the maximum electric field strength (V/m) that does not cause breakdown in the material.

Jammed state is used to describe the condition where relative motions between two adjacent parts, sheets, or structures is resisted by the introduction of an external pressure that squeezes the adjacent parts, sheets, or structures together. The relative motion refers to sliding motion, rotating motion, or translational motion between two adjacent parts, sheets, or structures in the jamming device. There is a spectrum of "jammed" intensity, which requires different forces to overcome the resistance to motion. The external pressure causing the jamming can come from a mechanical source, or application of a vacuum (so atmospheric pressure presses sheets together), from electrostatic attraction between sheets, or the like. Unjammed state, also referred to as loose state, is used to describe the condition where relative motions between adjacent sheets are not given additional resistance.

FIG. 1A is a cross-section schematic view of a jamming device 100A. The jamming device 100A includes a first sheet 110, a second sheet 120, and a dielectric layer 130A. The first sheet 110 includes a first conductive layer 115. The second sheet 120 includes a second conductive layer 125. The dielectric layer 130A is disposed between the first conductive layer 115 and the second conductive layer 125. In some implementations, the first sheet 100 and the second sheet 120 are non-extensible and flexible. In some cases, the first sheet 100 and the second sheet 120 are movable (e.g., slidable, rotatable) relative each other in a loose state and are not movable with each other in a jammed state, where a voltage (V) is applied to the jamming device 100A. As illustrated, the high potential V+ is applied to the first conductive layer 115 and the low potential V− is applied to the second conductive layer 125. In some cases, the jamming device 100A can be induced to a jammed state with a low voltage.

In some embodiments, the conductive layer (115, 125) can include a metal (e.g., copper, aluminum, steel), which can be annealed or hardened, laminated metal layers or foils (e.g., of the same or different metals); a conductive polymer, or a material filled with conductive particles such as carbon. In some embodiments, the sheet (110, 120) can include a support layer. The support layer can be made from paper or other fibrous material, a polymeric material (e.g., polyurethanes, polyolefins), a composite material (e.g., carbon fiber), an elastomer (e.g., silicone, styrene-butadiene-styrene), or other materials, and combinations thereof. In some cases, the support layer has a thickness no less than 50 micrometers. In some cases, the support layer has a thickness no less than 125 micrometers. In some cases, the support layer and the conductive layer can be combined into one layer. In some cases, the first conductive layer 115 is a coating on the first sheet 110. The conductive coating material may be, for example, copper, aluminum, silver, nickel, indium tin oxide, carbon, graphite, or the like. In some embodiments, the dielectric layer can include silicon oxide, aluminum oxide, titanium oxide, mixed metal oxides, mixed metal nitrides, barium titanite, or polymers such as polyimide, acrylates, or the like. In some cases, the dielectric layer can be a dielectric film. In some cases, the dielectric layer 130A is a coating on the first sheet 110. The coating material can include silicon oxide, aluminum oxide, titanium oxide, mixed metal oxides, mixed metal nitrides, barium titanite, or polymers such as polyimide, acrylates, or the like.

In some cases, the dielectric layer 130 is very thin. In some cases, the dielectric layer 130 has a thickness (D) less than or equal to 10 micrometers. In some cases, the dielectric layer 130 has a thickness (D) less than or equal to 5 micrometers. In some cases, the dielectric layer 130 has a thickness (D) less than or equal to 1 micrometers. In some cases, the distance between the first conductive layer 115 and the second conductive layer 125 is no greater than 10 micrometers. In some cases, the jamming device is jammed with a low voltage. In some cases, the low voltage is no greater than 100V. In some cases, such voltage is less than or equal to a break-down voltage of a distance between the first and the second conductive layer.

Electrostatic jamming can be understood by modeling each set of adjacent oppositely charged conductive layers with dielectric material between them as a parallel plate capacitor. The opposite charge on those layers are attracted to each other. It can be shown that the attractive force creates a compressive pressure on the dielectric material that can be represented by Equation (2):

$$P = \frac{\varepsilon_r \varepsilon_0}{2} \frac{V^2}{d^2}, \tag{2}$$

where $\varepsilon_r$ is the relative permittivity (or dielectric constant) of the dielectric material, $\varepsilon_0$ is the permittivity of free space (or vacuum permittivity or electric constant, $8.854187817 \ldots \times 10^{-12}$ F/m), V is the voltage potential between the two conductive layers, and d is the distance between the two conductive layers (i.e., the thickness of dielectric material(s)).

In some cases, the total thickness of the dielectric material includes one or more layers of dielectric material, and may also include some air gap or debris that was trapped between the conductive layers. When multiple dielectric layers exist (including multiple films, coatings, air, debris, etc) they can be modeled in series. In this case each layer can be modeled as a capacitor with capacitance $$C = \frac{\varepsilon_r \varepsilon_0 A}{d},$$

where A is the total area, d is the thickness of that layer, and $\varepsilon_r$ is the relative permittivity of that layer. The total capacitance of the layers in series can be calculated as $$\frac{1}{C_{tot}} = \frac{1}{C_1} + \frac{1}{C_2} + \frac{1}{C_3} + \ldots,$$

where $C_{tot}$ is the total capacitance and $C_1$, $C_2$ . . . are the capacitance of the individual layers. The total jamming pressure on the stack of dielectric material can be calculated as Equation (3):

$$P = \left(\frac{C_{tot}}{A}\right)\frac{V^2}{2(d_{tot})}, \tag{3}$$

where P is the pressure on the stack of dielectric material, $C_{tot}$ is calculated above, $d_{tot}$ is the total thickness of the dielectric layers (i.e., the distance between adjacent two conducting layers). An average relative permittivity for this space between conducting layers can also be calculated as Equation (4):

$$\varepsilon_{ave} = \frac{d_{tot} C_{tot}}{A \varepsilon_0}. \tag{4}$$

The electrostatic jamming allows sliding motion, both translational and rotational, between oppositely charged conductive layers. The sliding interface can exist between a conductive layer and a dielectric layer, or between a dielectric layer and another dielectric layer. There may be more than one slidable interface between two adjacent oppositely charged conductive layers. When voltage is applied, the pressure created causes the surfaces of the slidable interface to press against each other and resist motion. The resistance to motion can be modeled by considering two interdigitated sets of sheets being jammed together. The resistance to sliding two uniform sets of electrostatically jammed sheets apart can be calculated as Equation (5):

$$F = PA\mu N \tag{5}$$

where F is the force required to pull the sets apart (or push them together), A is the area of overlap between the sheets (the capacitor area), $\mu$ is the coefficient of friction at the sliding interfaces, and N is the total number of interfaces. This is a simplified model, since the areas, frictions and material properties may not be constant, but it is useful to show the primary factors in electrostatic jamming.

It is desireable to have a large jamming pressure that can resist significant forces. For many applications, it is desireable to utilize a very low voltage, which increases the safety, and reduces the cost and energy consumption of the controlling electronics. The jamming performance (i.e., jamming pressure) at very low voltage, according to Equation (2), can be improved by increasing the relative permittivity of the dielectric layers, and by reducing the distance between conductive layers. Using very thin dielectric layers, on the order of a few micrometers or less than one micrometer can enable significant jamming pressures at extra low voltage levels. For example, the International Electrotechnical Commision defines an extra low voltage device to be one that does not exceed 120V d.c. Other standards in the U.K. and USA define extra-low voltage systems as not exceeding 75V d.c. or 60V d.c. Based on the calculations earlier, a pressure approximately 10% of atmospheric pressure can be achieved at 120V if the total thickness of dielectric layers is around 4.4 micrometers (assuming an average relative permittivity of 3). One of the challenges of extra low voltage electrostatic jamming, is that the jamming pressure is reduced by the square of the distance between adjacent oppositely charged conductive layers. If debris or significant airgaps exist in the slidable interface between the conductive layers, the jamming pressure can become too low to achieve a useful resistance to motion, or even to pull the layers together. For example, only 1% of atmospheric pressure is achieved at 120V if the 4.4 micrometer distance above is increased to around 9.6 micrometers by adding a 5.2 micrometer airgap. Therefore, a small dielectric distance is need for appropriate jamming pressure for a jamming device operating at a low voltage. Additionally, an airgap not only increases the total dielectric distance, but also reduces the average relative permittivity causing an even greater reduction in the jamming pressure, according to the above equations. Some embodiments of the present disclosure enable extra low voltage jamming by using very thin dielectric layers and introducing an urging means to bring the sheets together to reduce airgaps.

In some cases, the jamming device 100A includes more than two sheets. The jamming device 100A includes one or more urging elements configured to keep the first conductive layer and the second conductive layer close to each other. In some cases, the one or more urging elements is an enclosure that the sheets of the jamming device 100A are disposed within. In some cases, the urging elements are spring elements, such as foam or elastic layers that exert a small pressure on the layers so they maintain light contact and can then be close enough to be jammed together with the application of voltage. In some cases, the gap between conductive layers is filled completely with dielectric material and only a minimal amount of air or other material.

In some cases, the dielectric layer 130A covers less than one hundred percent (100%) of a circumference of the first sheet 110. In other words, the jamming device 100 has the first conductive layer 115 exposed at a portion of or the entire edge of the sheet 100, which is not covered by dielectric materials at the edge. The exposed conductive layers can facilitate electrical connections. In some cases, the dielectric layer 130A covers less than eighty percent (80%) of a circumference of the first sheet 110. In some cases, the dielectric layer 130A covers less than sixty percent (60%) of a circumference of the first sheet 110. One challenge for electrostatic jamming devices is protecting the device from electrical breakdown (or dielectric breakdown) of air. Some existing electrostatic jamming devices have used high voltages, from several hundred volts to several thousand volts. This requires the jamming device to include continuous dielectric layers that extended far beyond the conductive layers so that the shortest path between conductive layers in air is many times longer than the path between conductive layers through the dielectric layer. This is because the dielectric strength of air at most voltages is only 3 MV/m, while many dielectric materials (such as polyethylene or polyimide) have dielectric strengths of 100 or more My/m. Some embodiments of the present disclosure, including the one illustrated in FIG. 1A, solves that problem by enabling useful jamming pressure with field strengths below the breakdown strength of air. Additional benefit is gained from the fact that the actual breakdown strength of air increases significantly at small gap distances, particularly below 10 micrometers. By operating below the breakdown voltage of air, some embodiments of the present disclosure enable a low cost efficient method of manufacture, where large master rolls of material can be created. Those rolls might include a structural layer, one or more conductive layers, and one or more dielectric layers. The rolls of material can then be cut into many smaller sheets of any shape, connected electrically, constrained mechanically as described later, and assembled into finished products. Because the electrostatic sheet jamming device is operated at a voltage less than the breakdown voltage of air for the thickness of the dielectric material between adjacent oppositely charged conductive layers, such jamming device is protected from electrical breakdown of air that can appear as electric arcing (or arc discharge) and cause melting or burning of material. Another advantage of some embodiments of the present disclosure is immunity to small pinholes or cuts or other imperfections in the dielectric layer. At high voltages, even a small pinhole can cause an electric arc. Some embodiments of the present disclosure enables not only the outer perimeter of jamming sheets to be cut without an extended dielectric layer, but it also enables complex patterns to be cut into the jamming sheets that increase the conformability of the sheets and enable other advantages presented later.

Figure 1B:
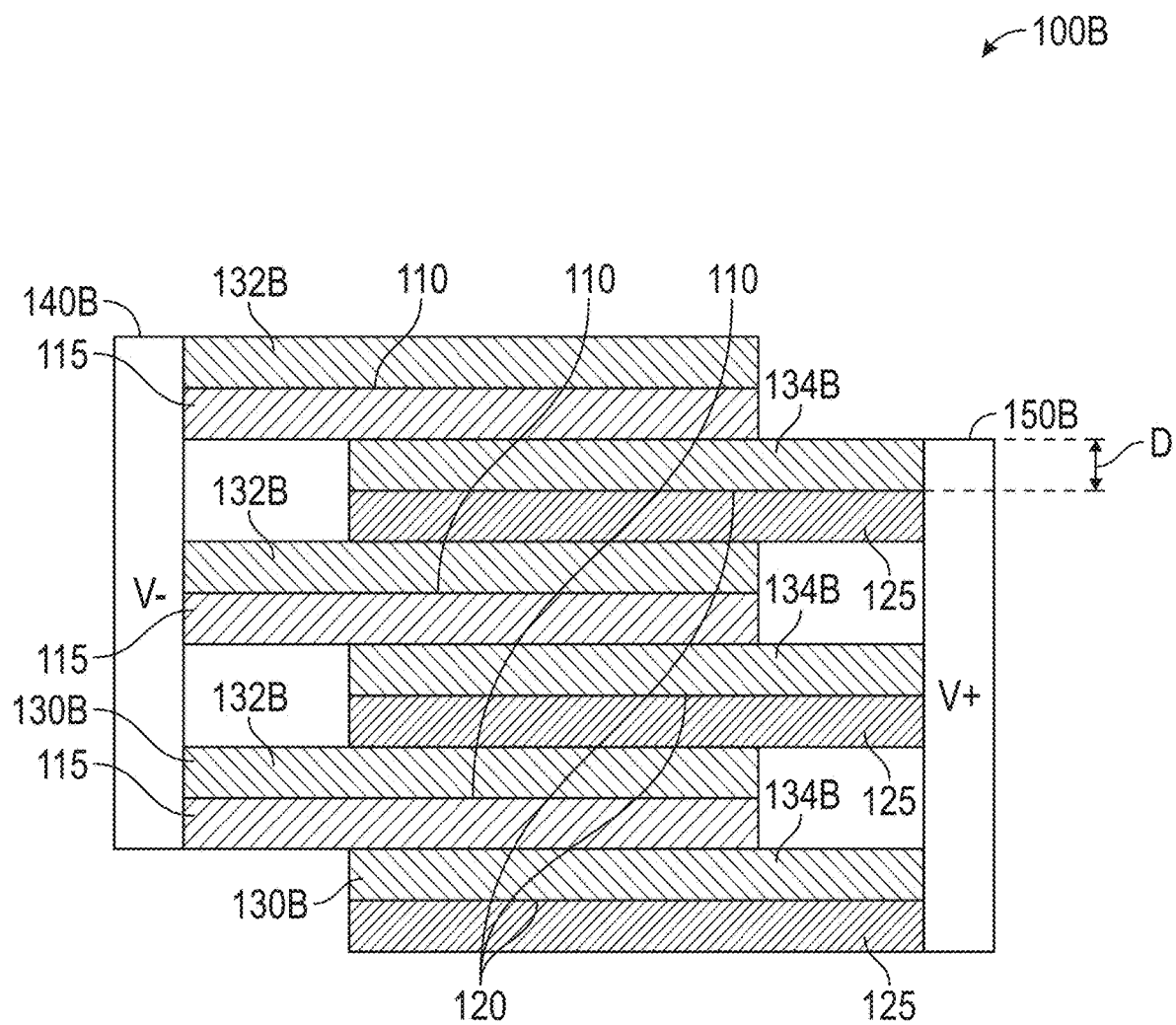
Figure 1C:
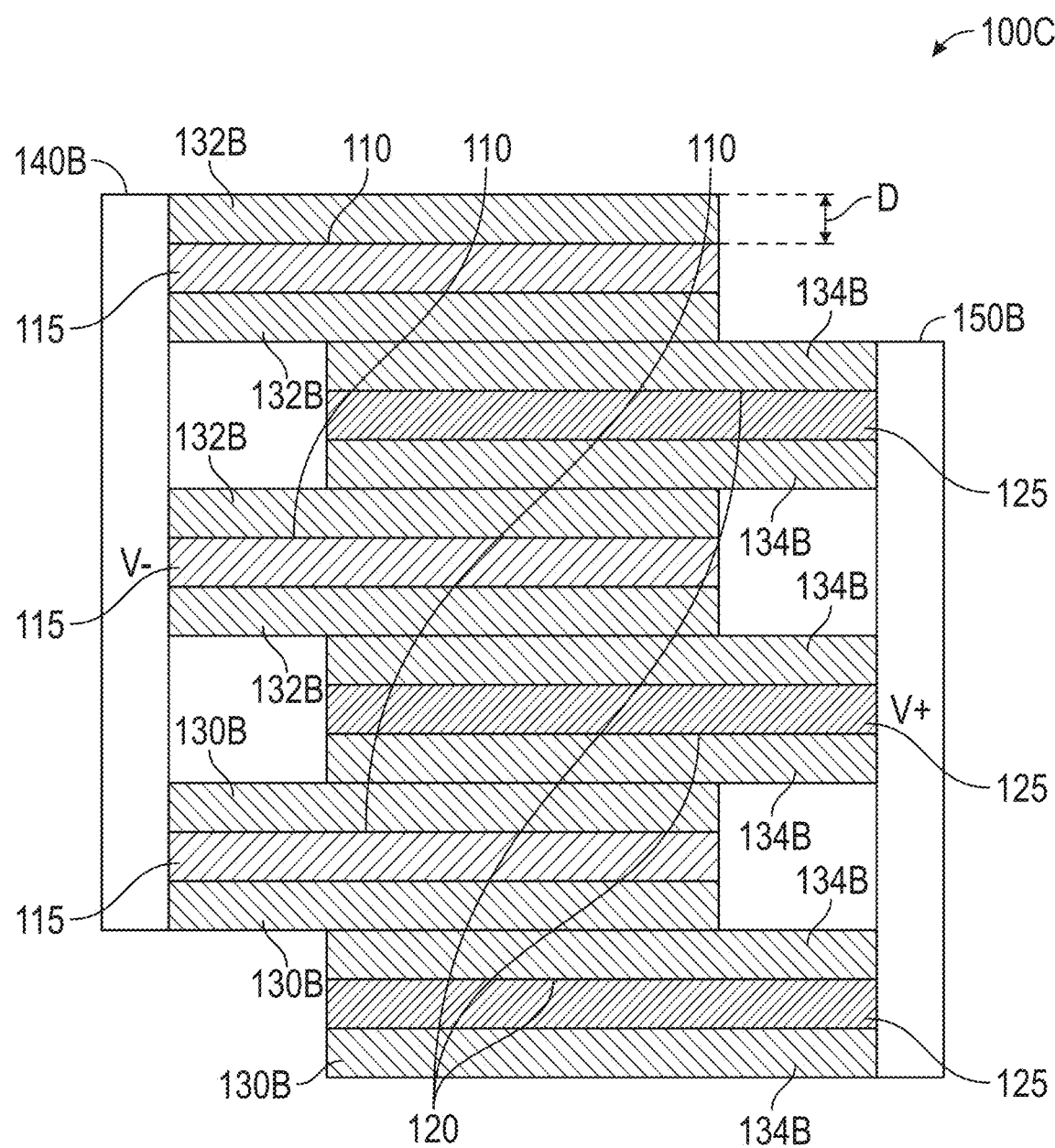

In some embodiments, the jamming device 110A can include multiple sheets, as the examples illustrated in FIGS. 1B and 1C and described in further detail below. In some cases, the sheets can be solid or patterned, e.g., to improve the flexibility (bendability) and/or the extensibility of the sheet. In some embodiments, the sheets have patterns to increase the flexibility along one or two axes but to have a desired stiffness along a third axis. In some embodiments, the sheets have patterns cut into them to make them extensible along one or two axes or to allow regions of the sheet to move in plane or along a surface relative to other regions. The patterning can be formed by a variety of methods, including but not limited to, steel rule die cutting, extrusion, molding, laser cutting, water jetting, machining, stereolithography or other 3D printing, laser ablation, photolithography, chemical etching, rotary die cutting, stamping, other suitable negative or positive processing techniques, or combinations thereof. Solid and patterned sheets of the present disclosure can be single or multi-layer constructions and can be formed of a variety of materials and layers of materials as described above.

In some embodiments, a jamming device includes two sets of sheets, each set includes multiple sheets. FIG. 1B illustrates one example of a jamming device 100B having two set of sheets. In the embodiment illustrated, the jamming device 100B includes a first set of sheets 110 and a second set of sheets 120, where the first set of sheets and the second set of sheets are interdigitated. Each of the first set of sheets includes a first conductive layer 115. Each of the second set of sheets includes a second conductive layer 125. The jamming device 100B further includes a set of dielectric layers 130B, where an adjacent pair of the first conductive layer 115 and the second conductive layer 125 has one of the set of dielectric layers 130B disposed in between. In some embodiments, the jamming device 100B includes a first connector 140B electrically conductively coupled to the first conductive layers 115 of at least part of the first set of sheets 110. In some cases, the jamming device 100B includes a second connector 150B electrically conductively coupled to the second conductive layers 125 of at least part of the second set of sheets 120. In some cases, the first set of sheets 110 and the second set of sheets 120 are movable relative each other in a loose state; and the first set of sheets 110 and the second set of sheets 120 are jammed with each other in a jammed state. In some cases, the jammed state is induced when a voltage less than or equal to 100V is applied between the first connector 140B and the second connector 150B, as illustrated. In some cases, the jammed state is induced when a voltage less than or equal to 200V is applied. In some cases, the jammed state is induced when a voltage less than or equal to a break-down voltage of air for the distance between adjacent conductive layers of one of the first set of sheets and one of the second set of sheets is applied between the first connector 140B and the second connector 150B.

In some embodiments, some dielectric layers 132B, which is a part of the dielectric layers 130, are coated on the first set of sheets. In some embodiments, some dielectric layers 134B, which is a part of the dielectric layers 130, are coated on the second set of sheets. In some cases, each of the dielectric layers is very thin. In some cases, the thickness of each of the dielectric layers is less than or equal to 10 micrometers. In some cases, the thickness of each of the dielectric layers is less than or equal to 5 micrometers. In some cases, the thickness of each of the dielectric layers is less than or equal to 1 micrometers. In some cases, a distance between the adjacent pair of the first conductive layer and one of the second conductive layer in a loose state is no greater than 10 micrometers. In some cases, a distance between the adjacent pair of the first conductive layer and one of the second conductive layer in a loose state is no greater than 10 micrometers. In some cases, a distance between the adjacent pair of the first conductive layer and one of the second conductive layer in a loose state is no greater than 5 micrometers.

In some cases, the first set of sheets 110 has a first longitudinal axis and the second set of sheets 120 has a second longitudinal axis, and the first longitudinal axis and the second longitudinal axis are parallel to each other. In some cases, the first longitudinal axis and the second longitudinal axis has an angle greater than 0°. In some cases, the first longitudinal axis and the second longitudinal axis has an angle proximate to 90°.

Figure 1D:
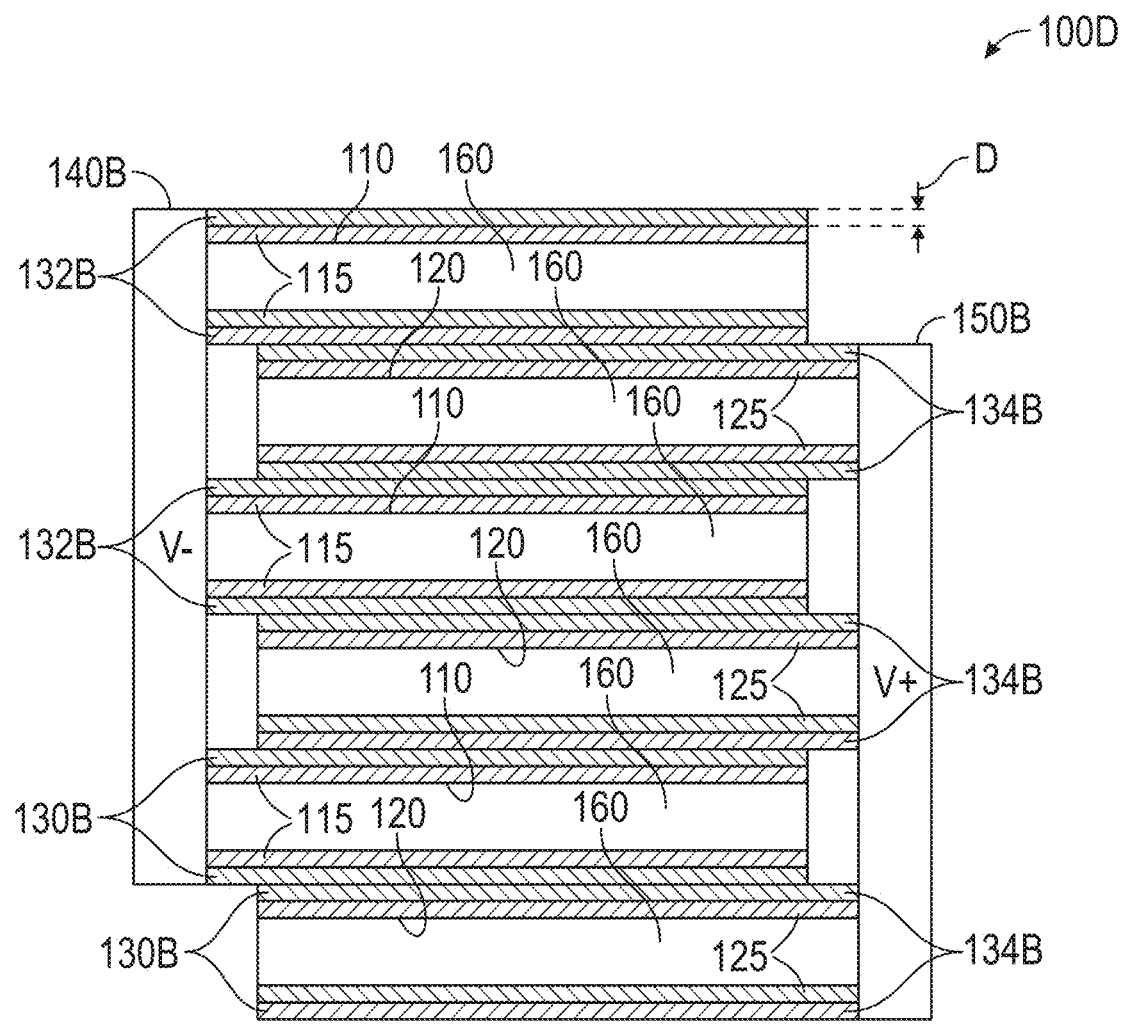
Figure 1E:
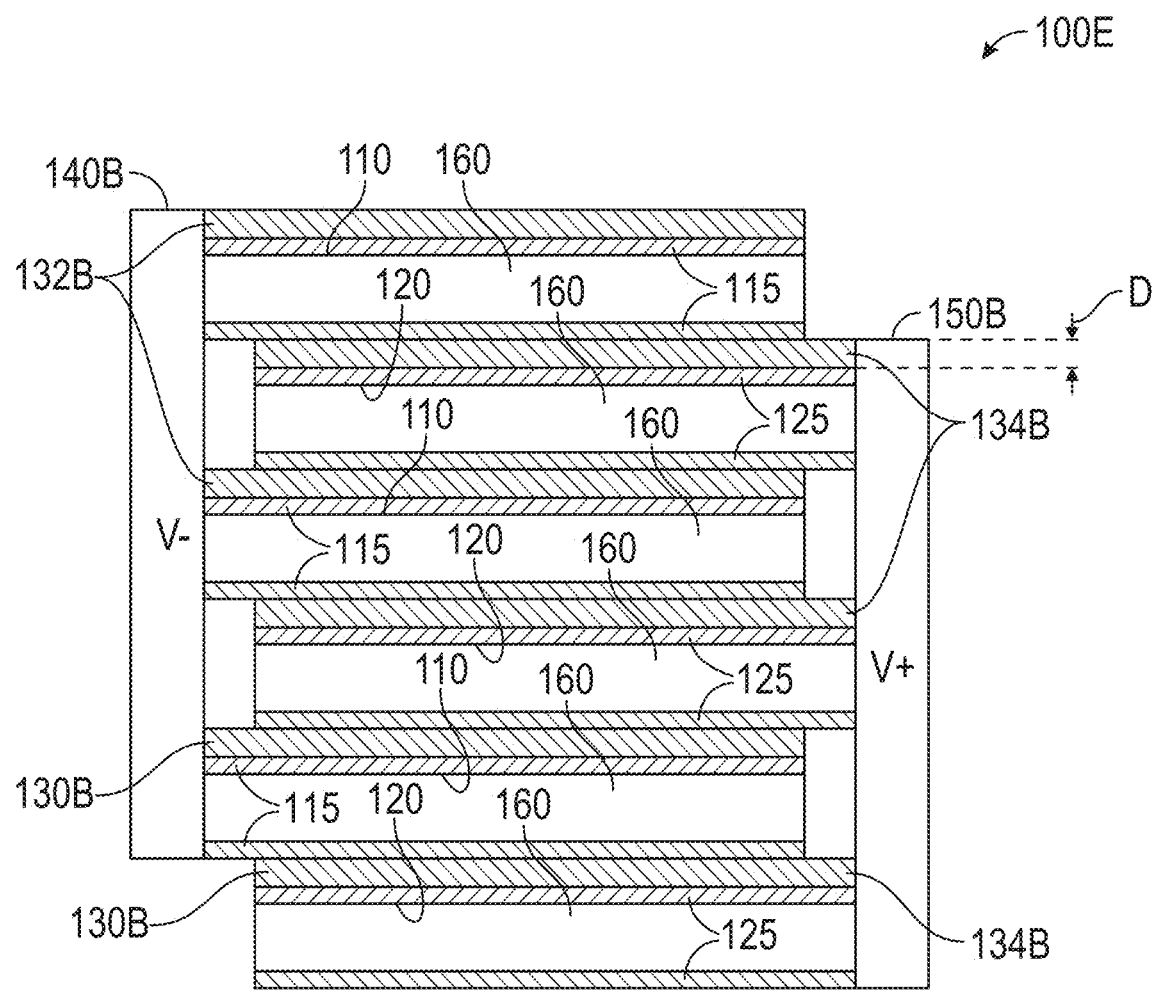

The conductive layers and dielectric layers can have various arrangements. One example arrangement of a jamming device 100C is illustrated in FIG. 1C, where each of the conductive layers is sandwiched between two dielectric layers, for example, the conductive layer 115 is sandwiched between two dielectric layers 132B and the conductive layer 125 is sandwiched between two dielectric layers 134B. In this arrangement, a slidable interface exists between two dielectric layers in the unjammed state, and the total dielectric thickness includes the dielectric layer 132B, the dielectric layer 134B, and possibly an air gap. Another example arrangement of a jamming device 100D is illustrated in FIG. 1D, where each of the conductive layers (115, 125) includes a core layer 160 with a conductive layer on both surfaces with a dielectric layer (132B, 134B) external to the conductive layer. This multiple layered construction can be constructed by stacking or laminating the layers. In some cases, the conductive layers are coated or deposited (chemical or physical vapor deposition, for example) onto the core layer. In some cases, the core layer 160 provides structural support. In some cases, the dielectric layers are coated or deposited (chemical or physical vapor deposition, for example) onto the conductive layers. One other example arrangement of a jamming device 100E is illustrated in FIG. 1E, where one of the conductive layers (115, 125) by the core layer 160 has an adjacent dielectric layer (132B, 134B).

Figure 1F:
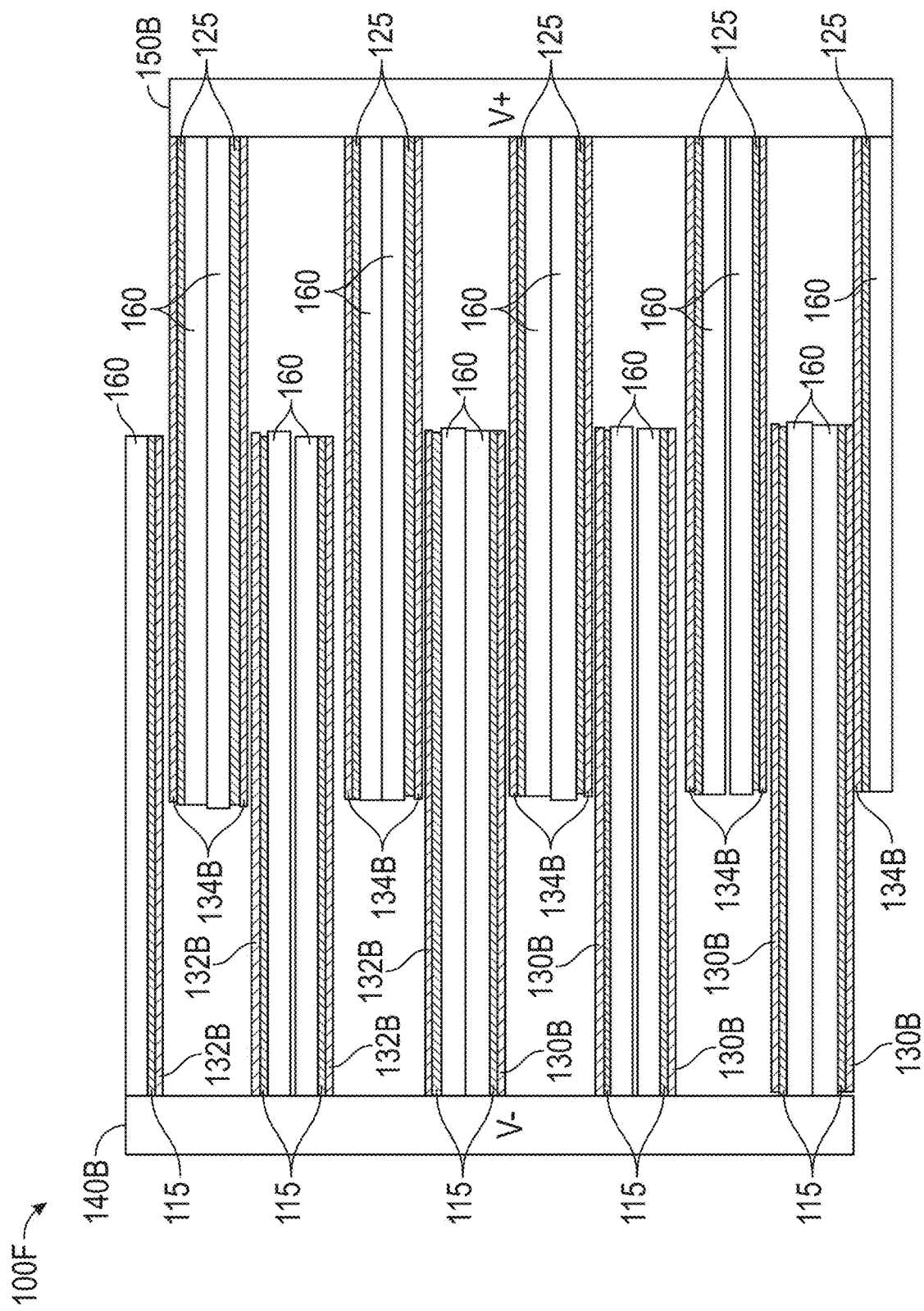

FIG. 1F illustrates one example of a jamming device 100F. The jamming device 100F includes jamming sheets (110, 120), each having a core layer 160, a conductive layer (115, 125) adjacent to the core layer 160, and a dielectric layer (132B, 134B) adjacent to the respective conductive layer. In some cases, the connector (140B and 150B) provide a mechanical as well as an electrical connection between the sheets. The connector can comprise tape, electrically conductive tape, conductive epoxy, conductive adhesive, conductive paste, elastomeric conductors, conductive or non-conductive thread, staples, clamps, rivets or other fasteners. The mechanical and electrical connection may be achieved by separate elements.

Figure 2A:
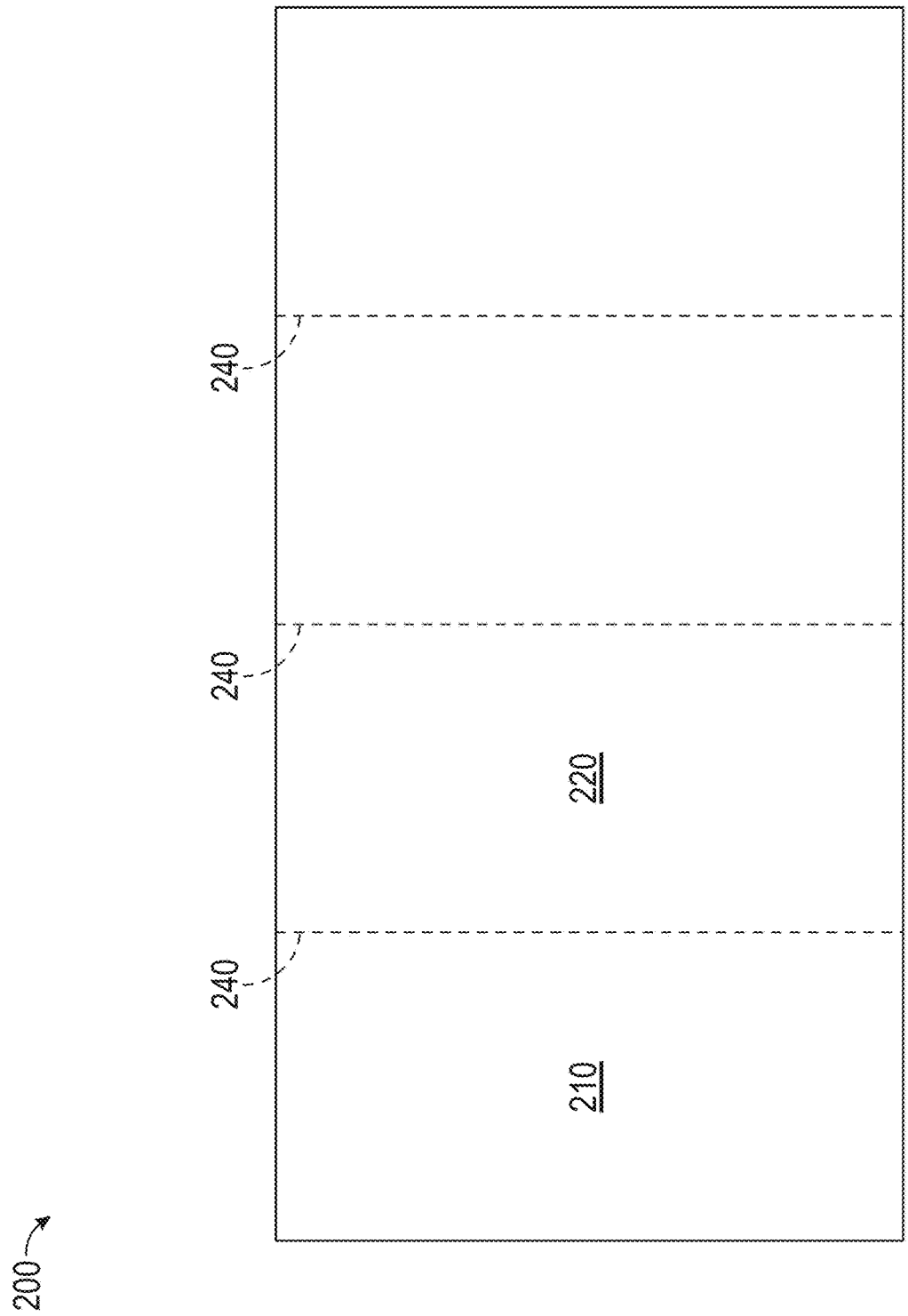
FIGS. 2A-2B illustrate examples of jamming sheets.
Figure 2B:
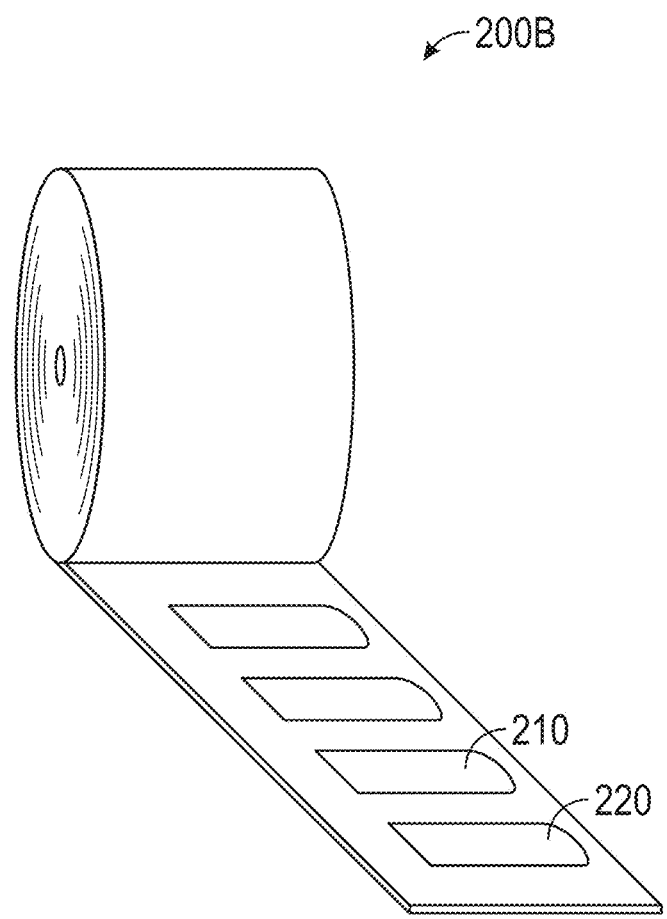
Figure 4A:
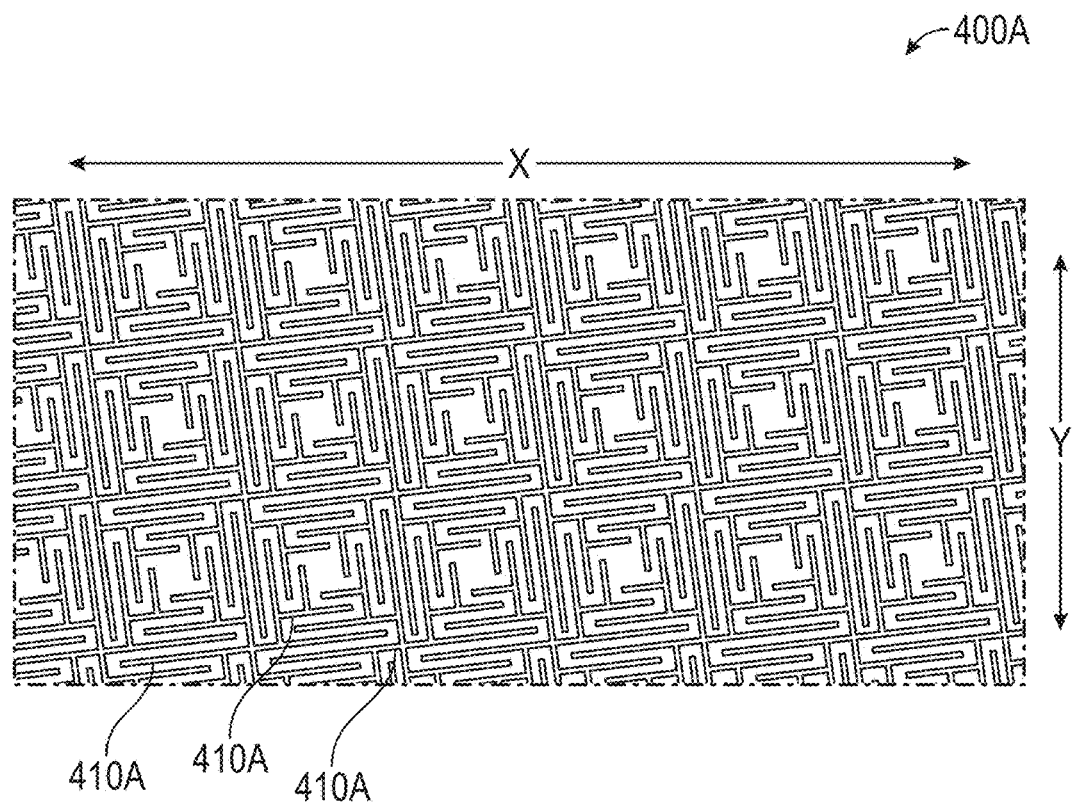
FIGS. 4A-4F illustrate some examples of jamming sheets having patterns and features.
Figure 4B:
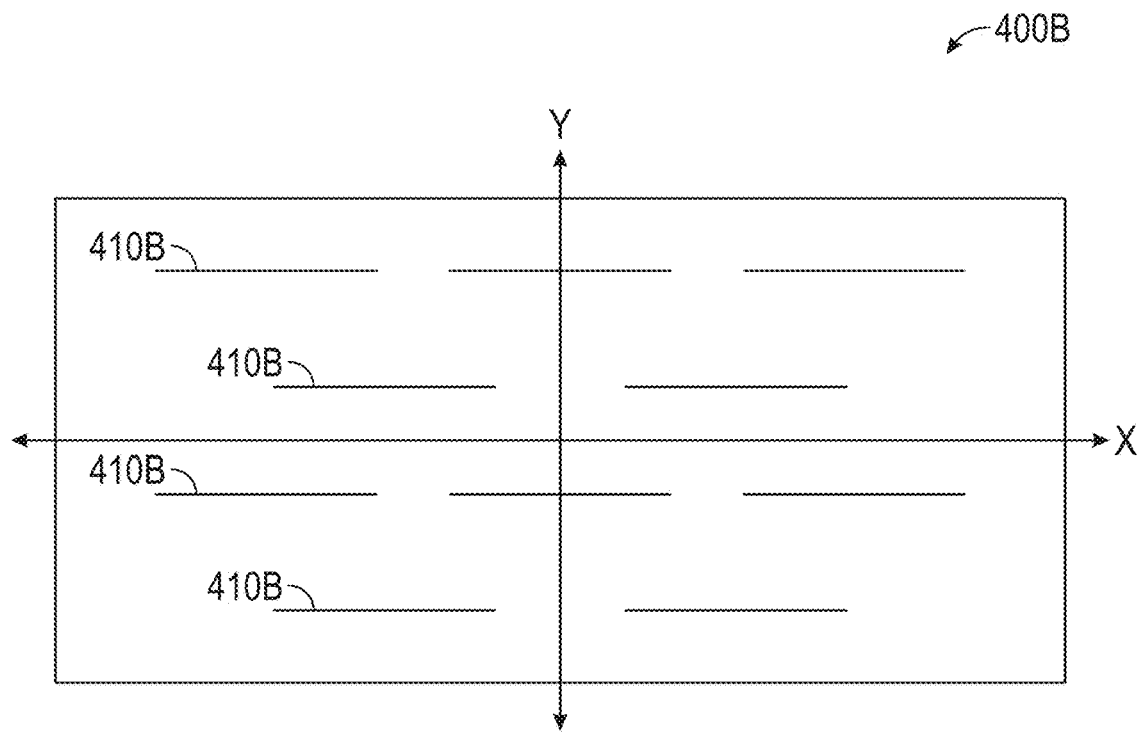

In some embodiments, the sheets in the jamming device can be provided in a tape form. In some cases, the tape is in a roll form. FIG. 2A illustrates one example of a jamming sheet 200 in a continuous tape form; FIG. 2B illustrates one example of a jamming sheet 220B in a roll form. The jamming sheets (200, 200B) may have any of the configurations and embodiments as described herein. In one example, the jamming sheet 200 has at least a conductive layer and a dielectric layer, for example, illustrated in FIGS. 1B-1E. In some cases, the jamming sheet includes a substrate or a core layer for support. In some cases, the jamming sheet may have patterns and features incorporated, for example, as illustrated in FIGS. 4A and 4B, and described in more details below.

In some embodiments, the jamming sheet (200, 200B) can be separated in a first section 210 and a second section 220. In some embodiments, the jamming sheet 200 includes lines of weakness 240 to allow easy separation of sections. In some cases, the dielectric layer has a thickness less than or equal to 10 micrometers. In some cases, the dielectric layer has a thickness less than or equal to 5 micrometers. In some cases, the dielectric layer has a thickness less than or equal to 1 micrometer. In some cases, the sheet (200, 200B) is non-extensible and flexible. In some embodiments, the first and second sections are removed from the jamming sheet 200B by die cutting, laser cutting, rotary die cutting, or other suitable techniques.

In some embodiments, a jamming device can be formed by the first section 210 of the sheet and the second section of the sheet 220. In some embodiments, the first section and the second section are movable relative each other in the loose state and are jammed with each other in the jammed state. In some cases, the jammed state is induced when a voltage is applied between the conductive layer of the first section and the conductive layer of the second section. In some cases, the applied voltage is less than or equal to a break-down voltage of a distance between the first and the second conductive layer. In some cases, the applied voltage is no greater than 100V.

In some cases, the applied voltage is no greater than 200V. In some cases, the distance between the conductive layer of the first section and the conductive layer of the second section is no greater than 5 micrometers. In some cases, the distance between the conductive layer of the first section and the conductive layer of the second section is no greater than 10 micrometers. In some embodiments, the dielectric layer is a coating on the sheet 200. In some embodiments, the conductive layer is a coating on the sheet 200.

Figure 3A:
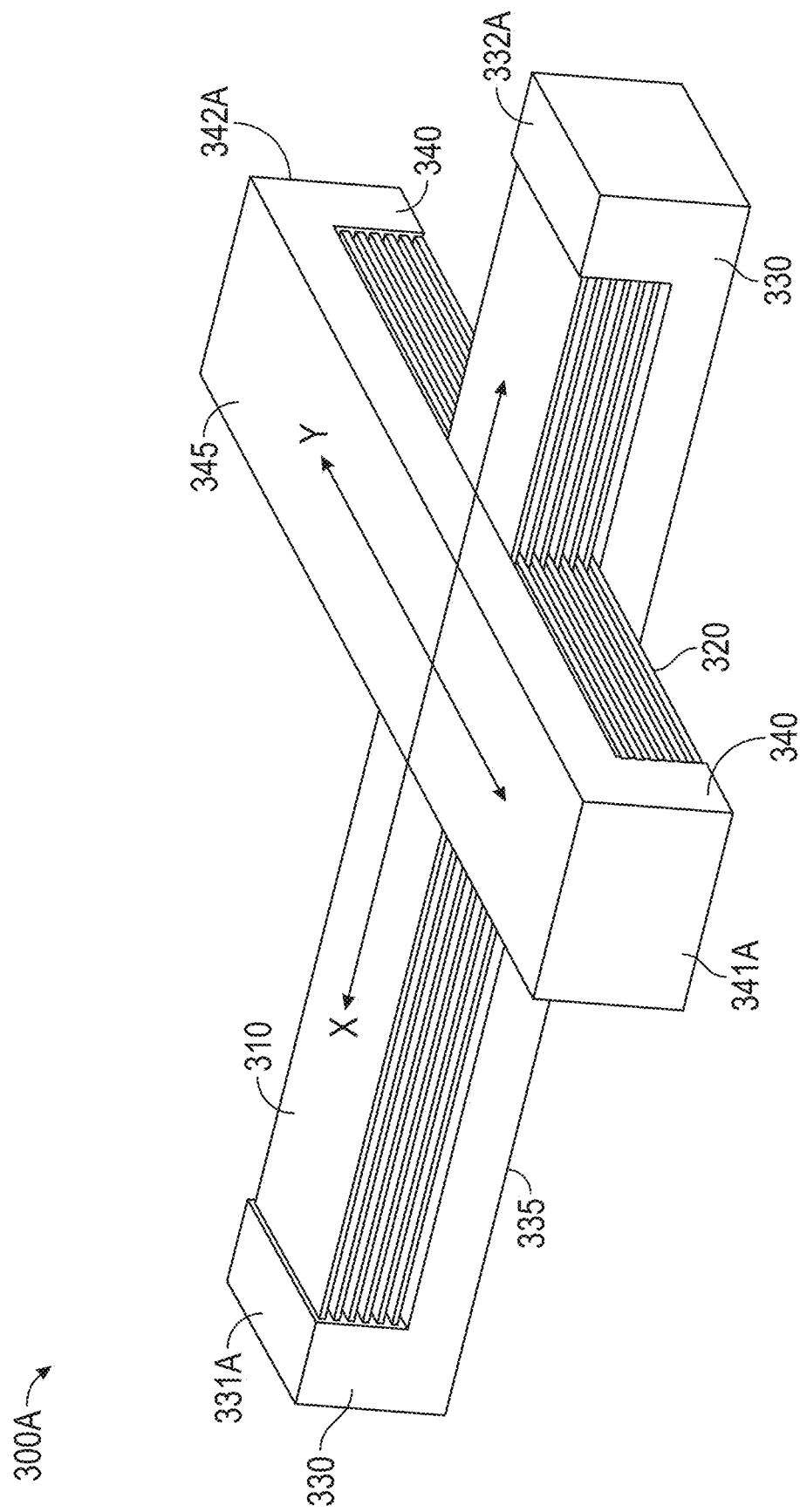
FIGS. 3A and 3B illustrate some examples of arrangements of jamming sheets in a jamming device.
Figure 3B:
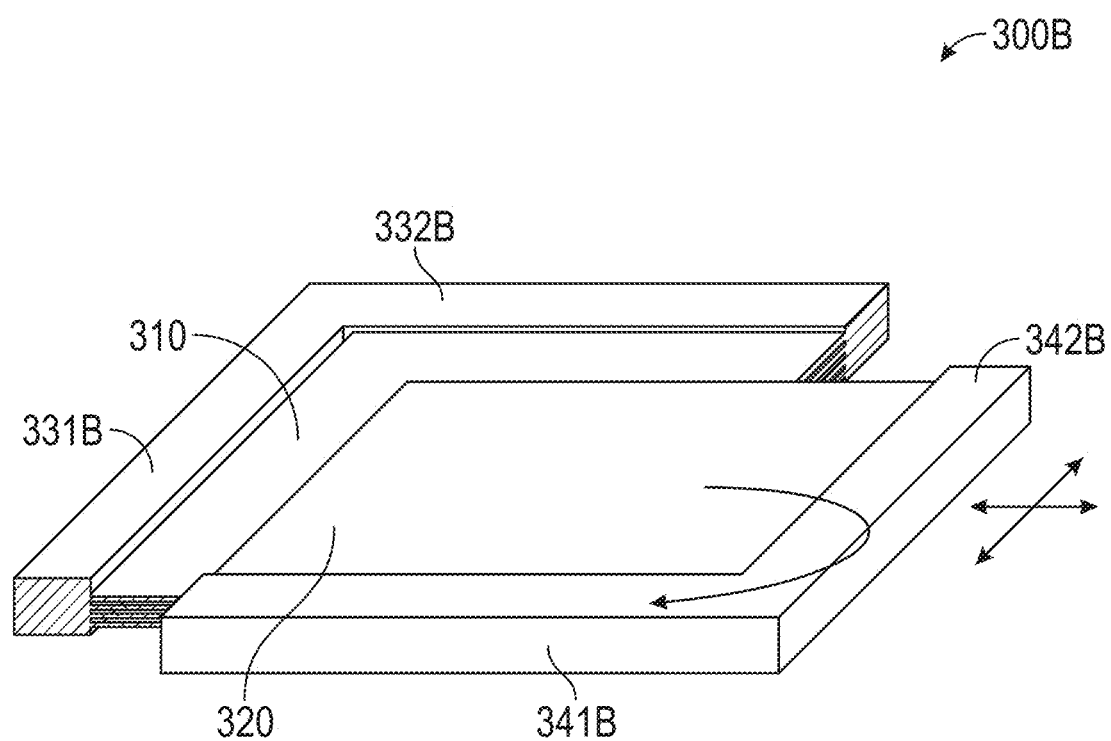

In some embodiments, the sheets are in various arrangements in a jamming device to achieve the desired functionality. In some cases, the sheets have a connector at one end, as illustrated in FIGS. 1B and 1C. FIGS. 3A and 3B illustrate some other examples of arrangements of jamming sheets in a jamming device. FIG. 3A illustrate two sets of jamming sheets (310, 320) arranged at an angle in a jamming device 300A. Each jamming sheet can have any of the configurations and embodiments as described herein. In some embodiments, each of the first set of jamming sheets 310 and the second set of jamming sheets 320 has a conductive layer. In some embodiments, each of the first set of jamming sheets 310 and the second set of jamming sheets 320 has a conductive layer and a dielectric layer. In some cases, the first set of jamming sheets 310 and the second set of jamming sheets 320 are interdigitated. In some cases, the jamming sheets are arranged such that a dielectric layer is disposed between two adjacent conductive layers. In some cases, the first set of jamming sheets 310 has connectors 330 on two edges, respectively 331A and 332A. In the example illustrated, the connectors 330 are at the two opposing edges. In some cases, the second set of jamming sheets 320 has connectors 340 on two edges, respectively 341A and 342A. In the example illustrated, the connectors 341A and 342A are disposed proximate to two opposing edges. In some cases, the connectors 330 and 340 are electrically coupled to the conductive layers of some or all of the jamming sheets (310, 320). In some cases, one of the two connectors (331A, 332A) is electrically coupled to the conductive layers of some or all of the jamming sheets 310. In some cases, one of the two connectors (341A, 342A) is electrically coupled to the conductive layers of some or all of the jamming sheets 320.

The first set of jamming sheets 310 has a longitudinal axis X and the second set of jamming sheets 320 has a longitudinal axis Y. In some cases, the axis X and the axis Y form a degree greater than 0° and less than 180°. In one embodiment, the axis X and the axis Y form a degree close to 90°. In one embodiment, the axis X and the axis Y form a degree about 45°. In one embodiment, the axis X and the axis Y form a degree about 130°. In one embodiment as illustrated, the connectors (330, 340) are connecting the shorter edges of the sheets. In some embodiments, the connectors are connecting the longer edges of the sheets.

In some embodiments, the first set of sheets 310 and the second set of sheets 320 are movable relative to each other in a loose state and jammed with each other in a jammed state. In some cases, the first set of sheets 310 and/or the second set of sheets 320 can be rotated in the loose state. In some cases, the jammed state is induced when a voltage is applied between the first connector and the second connector. In some cases, the applied voltage is no greater than 100V. In some cases, the applied voltage is no greater than 200V. In some cases, the applied voltage is less than or equal to a break-down voltage of a distance between the first and the second conductive layer. In some cases, a distance between the adjacent conductive layers in a loose state is no greater than 10 micrometers. In some cases, a distance between the adjacent conductive layers in a loose state is no greater than 5 micrometers.

In the embodiment illustrated in FIG. 3A, the jamming device 300A includes enclosures 335 and 345. In some embodiments, the enclosures 335 and 345 include the connectors 330 and 340. In some embodiments, the enclosures 335 and 345 are partially opened. In some embodiments, the enclosures 335 and 345 are configured to keep the jamming sheets 310 and 320 disposed close to each other. In some embodiments, the enclosures (335 and/or 345) are flexible. The enclosures 335 and 345 are examples of a means of urging the sheets into close proximity.

FIG. 3B illustrates another example of a jamming device 310B having two sets of jamming sheets (310, 320). Each jamming sheet can have any of the configurations and embodiments as described herein. In some embodiments, each of the first set of jamming sheets 310 and the second set of jamming sheets 320 has a conductive layer. In some embodiments, each of the first set of jamming sheets 310 and the second set of jamming sheets 320 has a conductive layer and a dielectric layer. In some cases, the first set of jamming sheets 310 and the second set of jamming sheets 320 are interdigitated. In some cases, the jamming sheets are arranged such that a dielectric layer is disposed between two adjacent conductive layers. In some cases, the first set of jamming sheets 310 has connectors proximate to two edges, respectively 331B and 332B. In the example illustrated, the connectors 331B and 332B are disposed proximate to two adjacent edges. In some cases, the second set of jamming sheets 320 has connectors 340 on two edges, respectively 341B and 342B. In the example illustrated, the connectors 341B and 342B are disposed proximate to two adjacent edges. In some cases, the connectors (331B, 332B, 341B, 342B) are electrically coupled to the conductive layers of some or all of the jamming sheets (310, 320). In some cases, one of the two connectors (331B, 332B) is electrically coupled to the conductive layers of some or all of the jamming sheets 310. In some cases, one of the two connectors (341B, 342B) is electrically coupled to the conductive layers of some or all of the jamming sheets 320. The connectors 331B, 332B, 341B, 342B can also comprise a means of urging the sheets to stay within close proximity of each other.

In some embodiments, the first set of sheets 310 and the second set of sheets 320 are movable relative to each other in a loose state and jammed with each other in a jammed state. In the example illustrated, the first set of sheets 310 and/or the second set of sheets 320 can be rotated or translated according to the arrows. In some cases, the jammed state is induced when a voltage is applied between the first connector and the second connector. In some cases, the applied voltage is no greater than 100V. In some cases, the applied voltage is no greater than 200V. In some cases, the applied voltage is less than or equal to a break-down voltage of a distance between the first and the second conductive layer. In some cases, a distance between the adjacent conductive layers in a loose state is no greater than 10 micrometers. In some cases, a distance between the adjacent conductive layers in a loose state is no greater than 5 micrometers.

In some embodiments, the sheets used in a jamming device may be a solid flat sheet. In some embodiments, the sheets used in a jamming device may be sheets having patterns, protrusions, slits, openings, and other features. In some embodiments, the sheets may include three dimensional structures but the sheets are generally flat. FIGS. 4A and 4B illustrate some examples of sheets having patterns and features. FIG. 4A illustrates a jamming sheet 400A having patterns. In some cases, the jamming sheet 400A is made of non-extensible materials. In some cases, the jamming sheet 400A includes a set of slit features 410A such that the sheet is extensible on an axis X. In some cases, the jamming sheet 400A includes a set of slit features 410A such that the sheet is extensible on an axis Y. In some cases, the jamming sheet 400A includes a conductive layer. In some cases, the jamming sheet 400A includes both a conductive layer and a dielectric layer.

FIG. 4B illustrates one other example of a jamming sheet 400B having patterns that can be used in a jamming device. In some cases, the pattern includes a set of slit features 410B that allow the sheet to be extensible in one axis, along axis Y for instance. In some cases, this extensibility gives the sheet increased conformability to bend out of plane along a path in that axis. For example, because of the extensibility along axis Y, the sheet in FIG. 4B could be more easily rolled into a cylinder whose axis is aligned along axis X than a sheet without the slits.

Figure 4C:
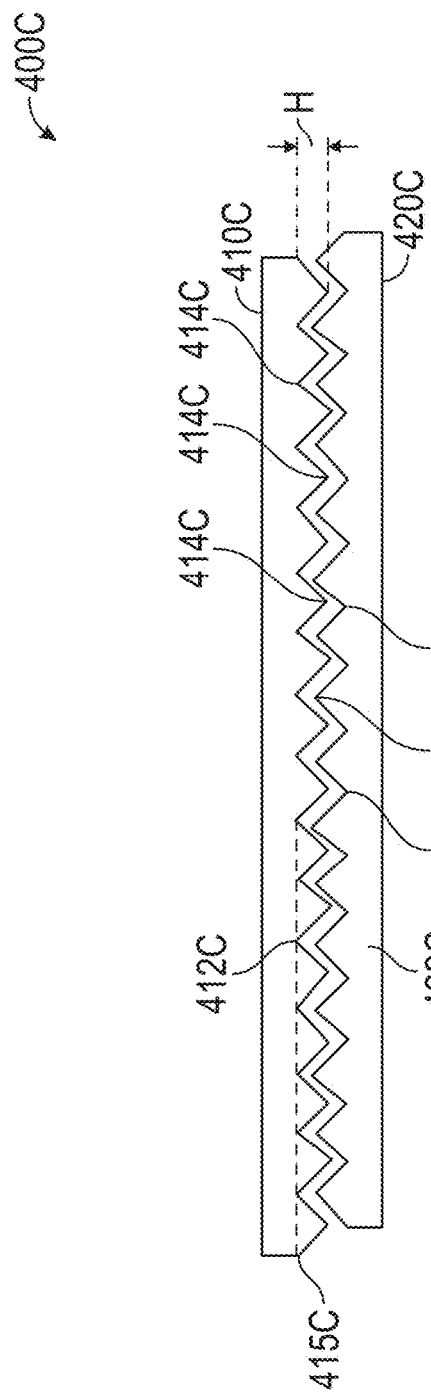
Figure 4D:
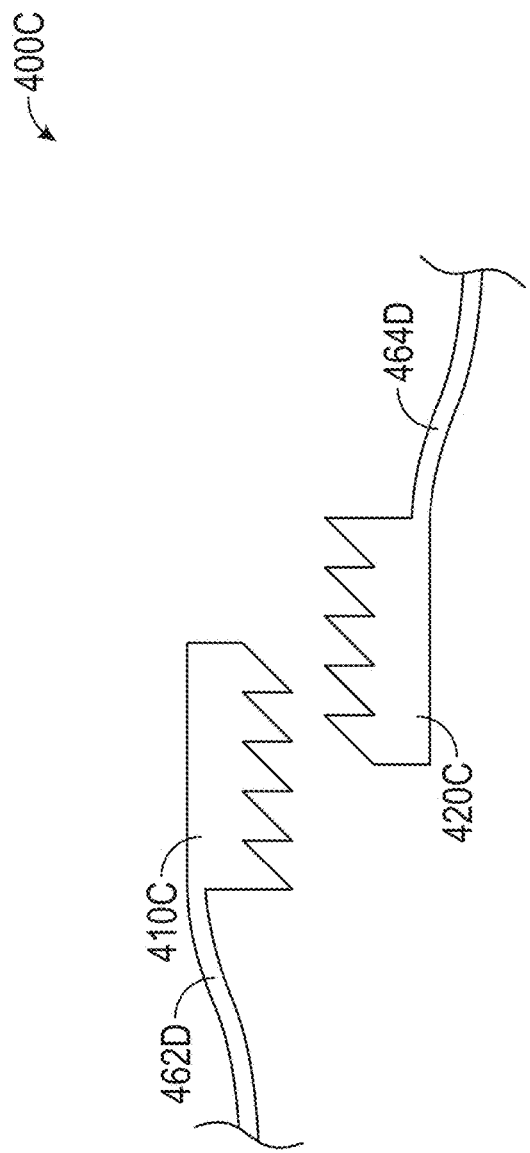

FIG. 4C illustrates a cross-sectional view of another example of jamming device 400C using jamming sheets 410C and 420C; and FIG. 4D illustrates the jamming sheets 410C and 420C when they are apart from each other. In some cases, the jamming sheet 410C includes a substrate 412C. In some cases, the substrate 412C has a general plane 415C. In some cases, the jamming sheet 410C includes a set of features 414C protruded from the substrate 412C. Similarly, the jamming sheet 420C may include a substrate 422C, and a set of features 424C protruded from the substrate 424C. In some cases, a jamming device may be formed by two or more jamming sheets 410C. In some cases, the set of features 414C and the set of features 424C are configured to mate with each other. In some cases, the jamming sheets 410C and 420C are non-extensible and flexible. In some cases, the jamming sheets 410C and/or 420C include a conductive layer. In some cases, the jamming sheets 410C and/or 420C include both a conductive layer and a dielectric layer.

In some cases, the set of features 414C and 424C have dimensions that are a few millimeters in length. In some cases, the features have dimensions that are less than one millimeter in length. In some cases, the features are a few micrometers to 50 micrometers in length. The height (H) of the set of features 414C refers to an average height of the set of features 414C from the general plane 415C. In some cases, the height of the set of features 414C is equal to or less than 10 millimeters. In some cases, the height of the set of features 414C is equal to or less than 1 millimeters. In some cases, the height of the set of features 414C is equal to or less than 50 micrometers. In some cases, each of the set of features is a prism, a pyramid, a rectangular protrusion, an ellipsoidal protrusion, a sawtooth, or a sinusoid protrusion. In some cases, the features do not change along one axis, as if they were extruded. In some cases, the features change along more than one axis, comprising discrete three-dimensional features. In some cases, the features repeat in patterns and in some cases, they are random. For example, random features with dimensions of a few microns or less can provide a desired coefficient of friction and can also provide some resistance to small debris particles.

In some embodiments, the jamming sheet 410C and the jamming sheet 420C are movable relative to each other in a loose state and jammed with each other in a jammed state. In some cases, the jammed state is induced when a voltage is applied to sheets. In some cases, the applied voltage is no greater than 500V. In some cases, the applied voltage is no greater than 50V. In some cases, the applied voltage is no greater than 100V. In some cases, the applied voltage is no greater than 200V. In some cases, the distance between adjacent conductive layers in the loose state is relatively large, allowing freedom of motion of the two sheets. The sheets can be attached to separate articles (462D and 464D) as shown in FIG. 4D. When the articles are brought together and the jamming sheets are placed in close proximity and a voltage applied to induce the jammed state, then the articles will resist moving apart. In some cases, the applied voltage is less than or equal to a break-down voltage of a distance between the conductive layers on the sheets. In some cases, a distance between the adjacent conductive layers in a loose state is no greater than 10 micrometers. In some cases, a distance between the adjacent conductive layers in a loose state is no greater than 5 micrometers. In some cases, some of the first features are mated with some of the second features in the jammed state. Mating of the features can create a significant increase in the resistance of the sheets to motion caused by shear forces. In some cases, the features are designed to increase the resistive force in specific directions.

Figure 4E:
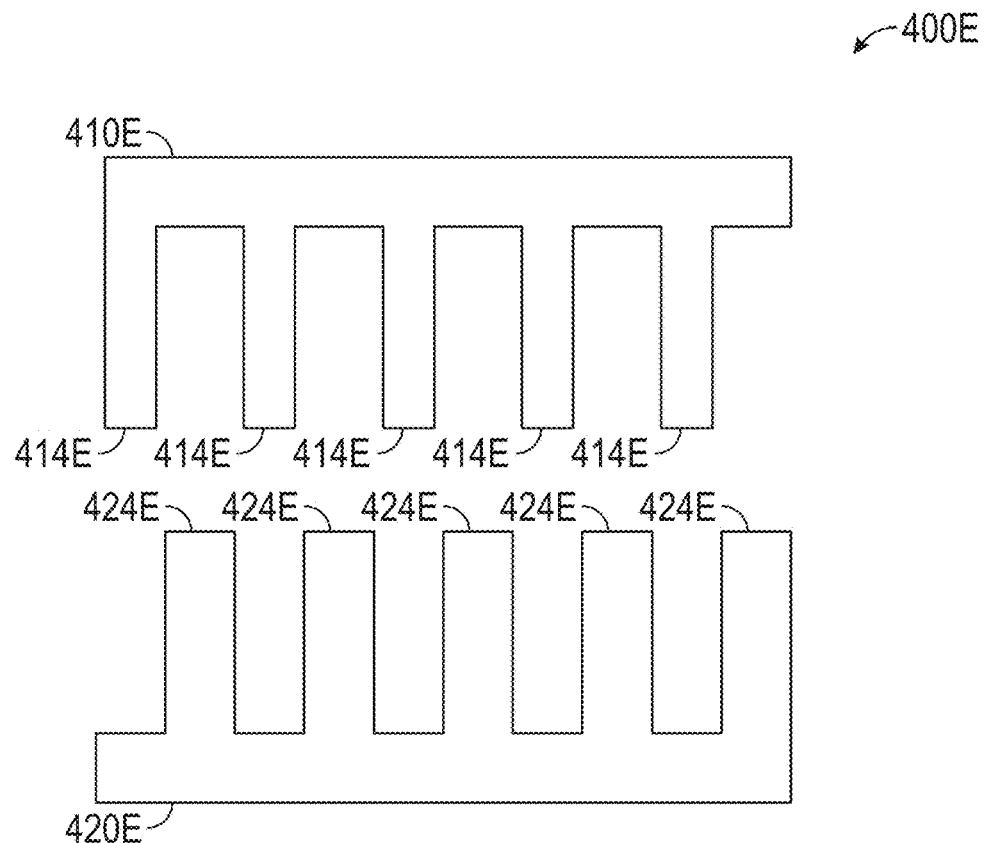

FIG. 4E illustrates a cross-sectional view of one example of jamming device 400E using jamming sheets 410E and 420E. In some cases, the jamming sheet 410E includes a substrate and a set of features 414E protruded from the substrate 412E. Similarly, the jamming sheet 420E may include a substrate and a set of features 424E protruded from the substrate. In some cases, a jamming device may be formed by two or more jamming sheets. In the example illustrated, the features (414E, 424E) are cylindrical or rectangular protrusions. In some cases, the set of features 414E and the set of features 424E are configured to mate with each other. In some cases, the jamming sheets 410E and 420E are non-extensible and flexible. In some cases, the jamming sheets 410E and/or 420E include a conductive layer. In some cases, the jamming sheets 410E and/or 420E include both a conductive layer and a dielectric layer.

Figure 4F:
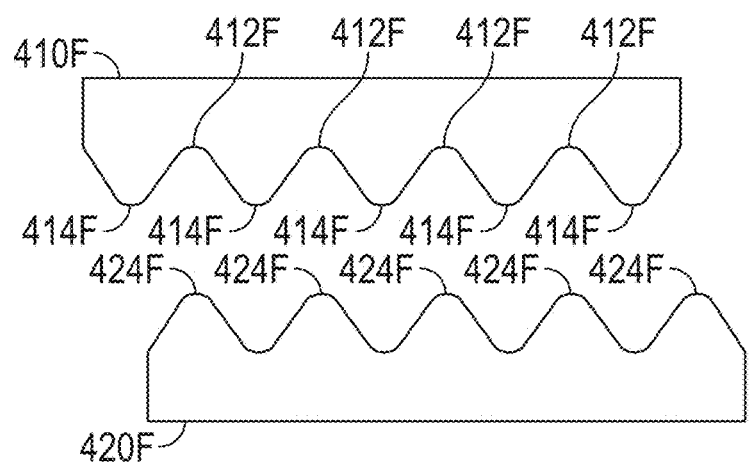

FIG. 4F illustrates a cross-sectional view of one example of jamming device 400F using jamming sheets 410F and 420F. In some cases, the jamming sheet 410F includes a substrate and a set of features 414F protruded from the substrate 412F. Similarly, the jamming sheet 420F may include a substrate and a set of features 424F protruded from the substrate. In some cases, a jamming device may be formed by two or more jamming sheets. In the example illustrated, the features (414F, 424F) are sinusoidal protrusions. In some cases, the set of features 414F and the set of features 424F are configured to mate with each other. In some cases, the jamming sheets 410F and 420F are non-extensible and flexible. In some cases, the jamming sheets 410F and/or 420F include a conductive layer. In some cases, the jamming sheets 410F and/or 420F include both a conductive layer and a dielectric layer.

Figure 4G:
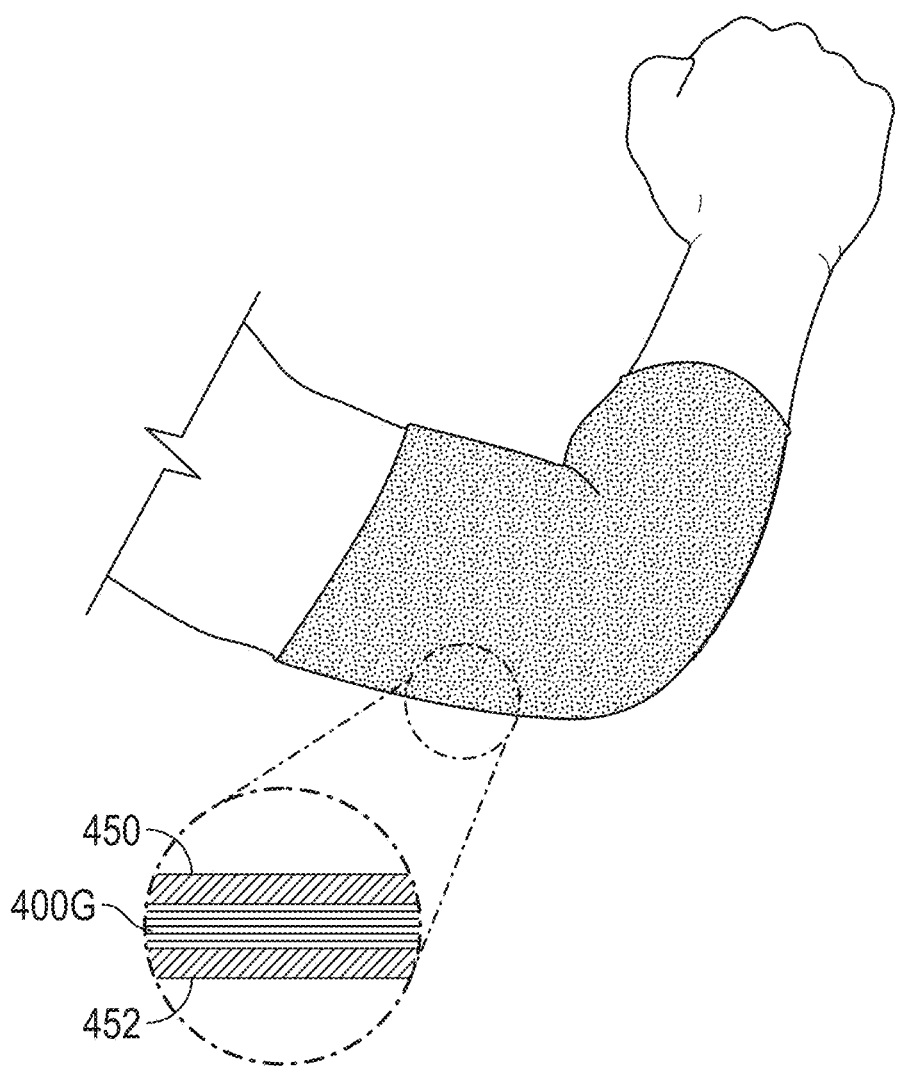
FIG. 4G illustrates one example of urging elements.

In some embodiments, the jamming device includes urging elements that urge the sets of sheets to remain close to one another in the loose, unjammed state. One example of urging elements is shown in FIG. 4G, where the urging elements include a highly compliant outer layer 452. In some cases, the urging elements include a highly compliant inner layer 450. In some cases, the urging elements is made of a stretchable material, for example spandex, or some elastic material. In some cases, the jamming sheets 400G are contained between the urging elements. In some cases, the jamming sheets 400G have patterns that allow them to be extensible in any axis such that they can conform to a complex surface, such as the human joint shown.

Figure 5A:
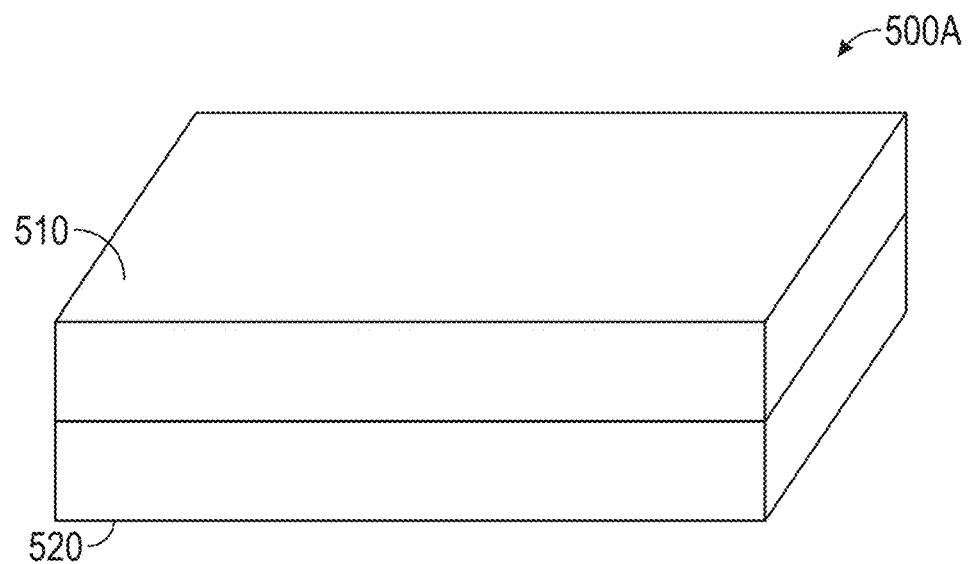
FIG. 5A illustrates one example of a flexible apparatus having a jamming device.

The jamming device may be used in various flexible apparatus and equipment to allow the apparatus/equipment to hold a bent position. FIG. 5A illustrates one example of a flexible apparatus 500A having a flexible component layer 510 and a jamming device 520. The flexible component layer 510 includes at least one component. The jamming device 520 may have any of the configurations and embodiments of a jamming device as described herein. In some cases, the jamming device 520 is disposed proximate to the flexible component layer 510. In some cases, the jamming device has a loose state and a jammed state, where the jamming device permits the flexible component layer to be bent in the loose state, and the jamming device is configured to resist bending of the flexible component layer in the jammed state.

Figure 5B:
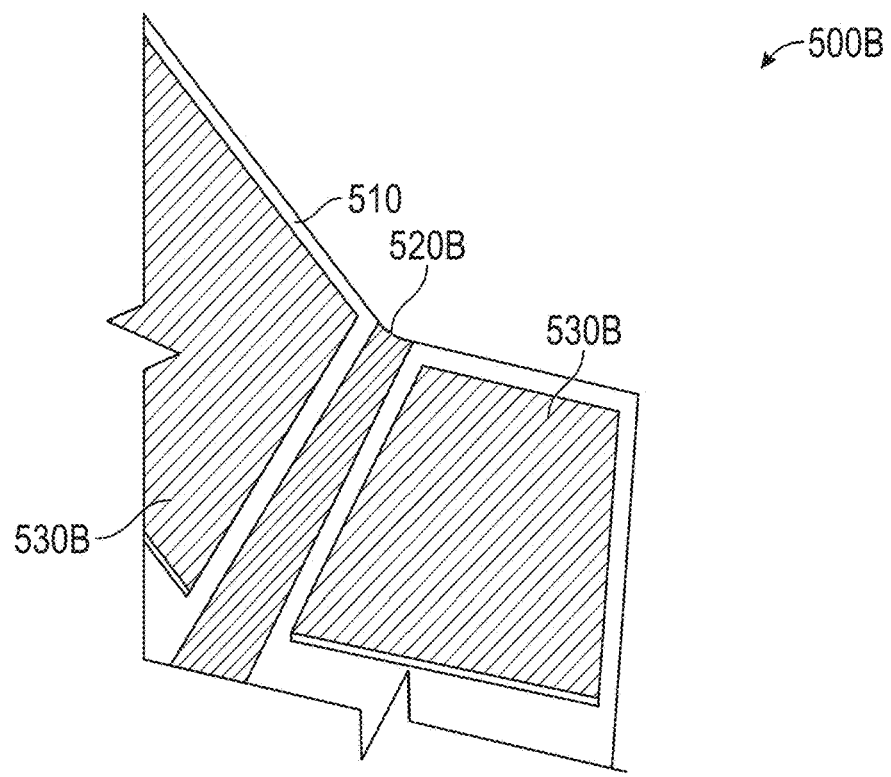
FIG. 5B illustrates one example a flexible display having a jamming device.

FIG. 5B illustrates one example of a display 500B using a jamming device 520B. In this example, the flexible component layer 510 is a flexible (or bendable) display, or referred to as a flexible display panel. The jamming device 520B may have any one of the embodiments and configurations of a jamming device as described herein. In some cases, the display panel 500B includes two rigid members 530B. As an example, the rigid member may also be a part of the heat sink, battery, electromagnetic shielding, or other components for the display panel 500B. The jamming device 520B is disposed proximate to the flexible component layer 510B. In some embodiments, the jamming device covers a majority of the surface of the flexible component layer.

In some cases, the jamming device can include one or more jamming elements disposed proximate to the flexible component layer, where each jamming element may have any of the configurations and embodiments of a jamming device as described herein.

Figure 6:
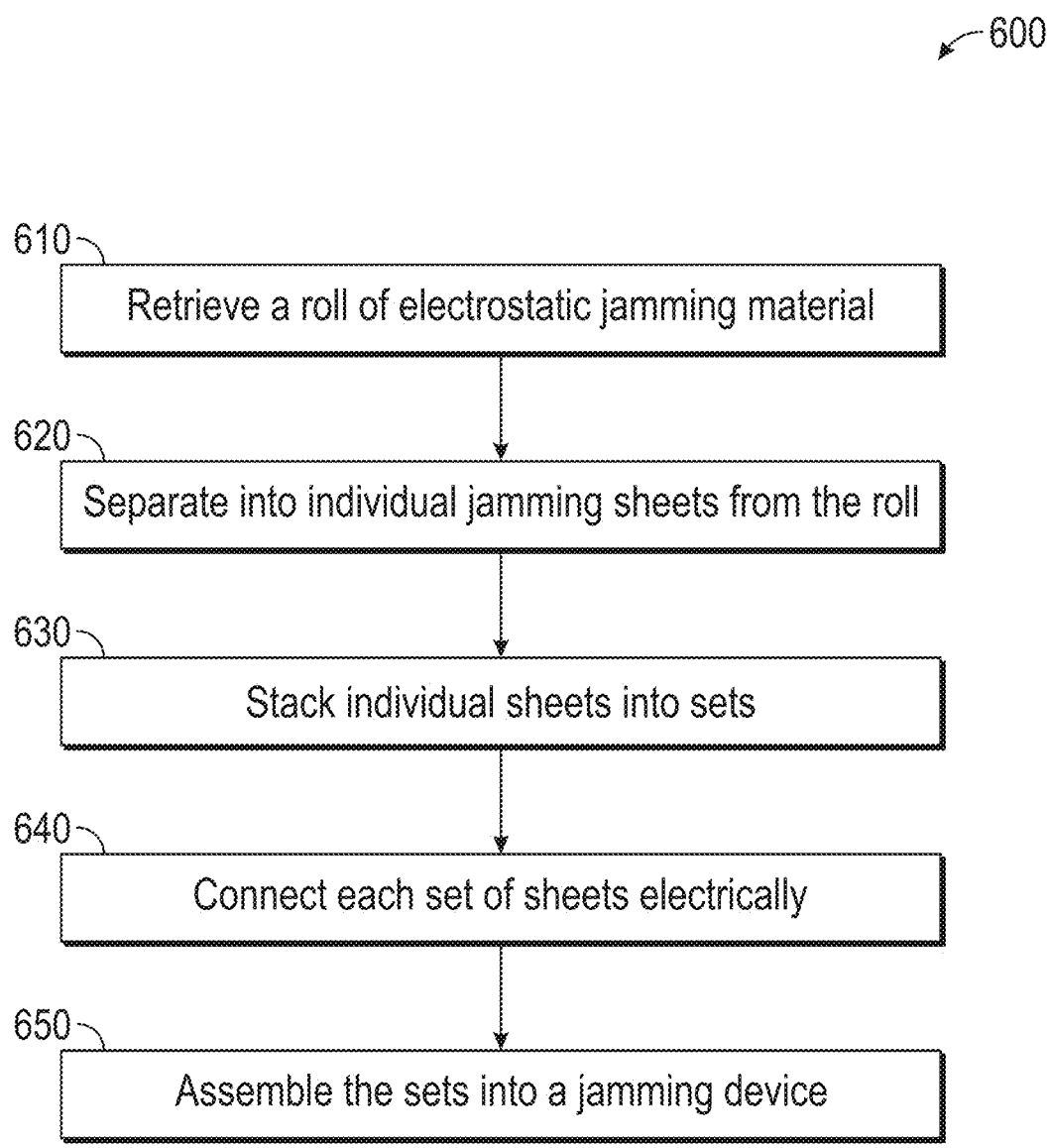
FIG. 6 illustrates a flow diagram of assembling an electrostatic jamming device.

FIG. 6 illustrates one example of flow diagram of assembling an electrostatic jamming device. One or more steps are optional. First, retrieve a roll of electrostatic jamming material (step 610). Separate into individual jamming sheets from the roll (step 620). The individual sheets can be separated by die cutting, laser cutting, rotary die cutting, or other suitable techniques. Stack individual sheets into two or more sets (step 630). Connect each set of sheets electrically (step 640). Assemble the two or more sets of jamming sheets into a jamming device (step 650). In some cases, the two or more sets of sheets are arranged to be interdigitated.

FIGS. 7A and 7B illustrate some examples of urging components, which can be used in a jamming device. FIG. 7A illustrates one example of an urging component 720A. As illustrated, the urging component is an enclosure with fixed clearance. In this example, the urging component does not add pressure to the jamming sheets 710. The jamming sheets can use any configurations and embodiments as illustrated and provided herein. FIG. 7B illustrates another example of an urging component 720B. As illustrated, the urging component 720B is a rivet style enclosure with fixed clearance. In this example, the urging component does not add pressure to the jamming sheets 710. In some embodiments, a compliant layer (such as a foam or spring) could be added into the clearance area to apply some small pressure on the sheets to urge them together.

EXEMPLARY EMBODIMENTS

Embodiment A1. An electrostatic sheet jamming device comprising a first sheet having a first conductive layer, a first dielectric layer disposed adjacent to the first conductive layer, a second sheet comprising a second conductive layer and disposed proximate to the first dielectric layer. The first dielectric layer is disposed between the first conductive layer and the second conductive layer. The first dielectric layer has a thickness less than or equal to 10 micrometers. The first sheet and the second sheet are non-extensible and flexible, wherein the first sheet and the second sheet are slidable relative to each other in a first state. The first sheet and the second sheet are jammed with each other in a second state when a voltage is applied between the first conductive layer and the second conductive layer. The applied voltage is less than or equal to a break-down voltage of air at a distance between the first conductive layer and the second conductive layer.

Embodiment A2. The jamming device of Embodiment A1, wherein the first dielectric layer is a coating on the first sheet.

Embodiment A3. The jamming device of Embodiment A1 or A2, further comprising a second dielectric layer, wherein the second sheet has a first surface and a second surface opposing the first surface, wherein the second conductive layer is on the first surface of the second sheet, and wherein the second dielectric layer is disposed proximate closer to the second surface of the second sheet than the first surface of the second sheet.

Embodiment A4. The jamming device of any one of Embodiments A1-A3, further comprising: a second dielectric layer disposed proximate to the second sheet.

Embodiment A5. The jamming device of any one of Embodiments A1-A4, wherein the second dielectric layer is coated on the second sheet.

Embodiment A6. The jamming device of any one of Embodiments A1-A5, wherein the applied voltage is no greater than 100V.

Embodiment A7. The jamming device of any one of Embodiments A1-A6, wherein the distance between the first conductive layer and the second conductive layer in the first state is no greater than 10 micrometers.

Embodiment A8. The jamming device of any one of Embodiments A1-A7, further comprising: one or more urging elements configured to keep the first conductive layer and the second conductive layer close to each other.

Embodiment A9. The jamming device of Embodiment A8, wherein the one or more urging elements comprise at least one of a highly compliant outer layer, a highly compliant inner layer, a fixed clearance limiting element, and a spring element.

Embodiment A10. The jamming device of any one of Embodiments A1-A9, wherein the first dielectric layer covers less than one hundred percent of a circumference of the first sheet.

Embodiment A11. The jamming device of any one of Embodiments A1-A10, wherein the first dielectric layer has a thickness less than or equal to 5 micrometers.

Embodiment A12. The jamming device of any one of Embodiments A1-A11, wherein a direct path between the first conductive layer and the second conductive layer for at least one part of the jamming device is approximately the same length as the distance between the first and second conductive layers in the second state.

Embodiment A13. The jamming device of any one of Embodiments A1-A12, wherein the first sheet is separated from a large sheet having a conductive layer.

Embodiment A14. The jamming device of Embodiment A13, wherein the large sheet is a roll of sheet.

Embodiment A15. The jamming device of any one of Embodiments A1-A14, wherein the first sheet is patterned such that it is extensible in at least one axis.

Embodiment A16. The jamming device of any one of Embodiments A1-A15, wherein the first sheet has patterned openings such that it is extensible in at least one axis.

Embodiment A17. The jamming device of any one of Embodiments A1-A16, wherein the first sheet has a plurality of protruded features.

Embodiment A18. The jamming device of Embodiment A17, wherein the second sheet has a plurality of protruded features.

Embodiment A19. The jamming device of Embodiment A18, wherein at least some of the plurality of protruded features of the first sheet are mated with some of the plurality of protruded features of the second sheet in the second state.

Embodiment A20. The jamming device of any one of Embodiments A1-A19, wherein the first dielectric layer has a relative permittivity greater than 3.

Embodiment A21. The jamming device of any one of Embodiments A1-A20, wherein the first dielectric layer comprises an inorganic compound.

Embodiment A22. The jamming device of any one of Embodiments A1-A21, wherein a coefficient of friction of the first sheet is less than 0.4.

Embodiment A23. The jamming device of any one of Embodiments A1-A22, wherein the first sheet comprises a core layer providing structural support.

Embodiment B1. An electrostatic sheet jamming device comprising a first set of sheets, each of the first set of sheets comprising a first conductive layer, a second set of sheets, each of the second set of sheets comprising a second conductive layer, a set of dielectric layers, a first connector electrically conductively connected to first conductive layers of at least part of the first set of sheets, and a second connector electrically conductively connected to second conductive layers of at least part of the second set of sheets. The first set of sheets and the second set of sheets are interdigitated. Each of the adjacent pair of the first set of sheets and the second set of sheets has one of the set of dielectric layers disposed in between. Each of the set of dielectric layers has a thickness less than or equal to 10 micrometers. The first set of sheets and the second set of sheets are slidable relative to each other in a first state. The first set of sheets and the second set of sheets are jammed with each other in a second state when a voltage is applied between the first connector and the second connector, where the applied voltage is less than or equal to a break-down voltage of air at a distance between adjacent conductive layers of one of the first set of sheets and one of the second set of sheets.

Embodiment B2. The jamming device of Embodiment B1, wherein at least some of the set of dielectric layers are coated on the first set of sheets.

Embodiment B3. The jamming device of Embodiment B2, wherein at least some of the set of dielectric layers are coated on the second set of sheets.

Embodiment B4. The jamming device of any one of Embodiments B1-B3, wherein the first set of sheets has a first longitudinal axis and the second set of sheets has a second longitudinal axis, and wherein the first longitudinal axis and the second longitudinal axis are generally parallel to each other.

Embodiment B5. The jamming device of any one of Embodiments B1-B4, wherein a distance between an adjacent pair of the first conductive layer and the second conductive layer in the first state is no greater than 10 micrometers.

Embodiment B6. The jamming device of any one of Embodiments B1-B5, wherein the first dielectric layer covers less than one hundred percent of a circumference of the first sheet.

Embodiment B7. The jamming device of any one of Embodiments B1-B6, wherein the applied voltage is no greater than 100V.

Embodiment B8. The jamming device of any one of Embodiments B1-B7, further comprising: one or more urging elements configured to keep the first set of sheets and the second set of sheets close to each other.

Embodiment B9. The jamming device of Embodiment B8, wherein the one or more urging elements comprise at least one of a highly compliant outer layer, a highly compliant inner layer, a fixed clearance limiting element, and a spring element.

Embodiment B10. The jamming device of any one of Embodiments B1-B9, wherein the first dielectric layer covers less than one hundred percent of a circumference of the corresponding sheet.

Embodiment B11. The jamming device of any one of Embodiments B1-B10, wherein at least one of the set of dielectric layers has a thickness less than or equal to 5 micrometers.

Embodiment B12. The jamming device of any one of Embodiments B1-B11, wherein the first set of sheets are separated from a large sheet having a conductive layer.

Embodiment B13. The jamming device of Embodiment B12, wherein the large sheet is a roll of sheet.

Embodiment B14. The jamming device of any one of Embodiments B1-B13, wherein at least one of the first set of sheets is patterned such that it is extensible in at least one axis.

Embodiment B15. The jamming device of any one of Embodiments B1-B14, wherein at least one of the first set of sheets has patterned openings such that it is extensible in at least one axis.

Embodiment B16. The jamming device of any one of Embodiments B1-B15, wherein at least one of the first set of sheets has a plurality of protruded features.

Embodiment B17. The jamming device of Embodiment B16, wherein at least one of the first set of sheets has a plurality of protruded features.

Embodiment B18. The jamming device of Embodiment B17, wherein at least some of the plurality of protruded features of at least one of the first set of sheets are mated with some of the plurality of protruded features of at least one of the second set of sheets in the second state.

Embodiment B19. The jamming device of any one of Embodiments B1-B18, wherein at least one of the set of dielectric layers has a relative permittivity greater than 3.

Embodiment B20. The jamming device of any one of Embodiments B1-B19, wherein at least one of the set of dielectric layers comprises an inorganic compound.

Embodiment B21. The jamming device of any one of Embodiments B1-B20, wherein a coefficient of friction of at least one of the first set of sheets is less than 0.4.

Embodiment B22. The jamming device of any one of Embodiments B1-B21, wherein at least one of the first set of sheets comprises a core layer providing structural support.

Embodiment C1. An electrostatic sheet jamming device formed by a sheet having a conductive layer and a dielectric layer. The jamming device includes a first section of the sheet, the first section being separated from the sheet, and a second section of the sheet, the second section being separated from the sheet. The sheet is non-extensible and flexible. The first section and the second section are slidable relative to each other in a first state. The first section and the second section are jammed with each other in a second state when a voltage is applied between a conductive layer of the first section and a conductive layer of the second section.

Embodiment C2. The jamming device of Embodiment C1, wherein the applied voltage is less than or equal to a break-down voltage of air at a distance between the first and the second conductive layer.

Embodiment C3. The jamming device of Embodiment C1 or Embodiment C2, wherein the applied voltage is no greater than 100V.

Embodiment C4. The jamming device of any one of Embodiments C1-C3, wherein a distance between the first section and the second section is no greater than 10 micrometers in the first state.

Embodiment C5. The jamming device of any one of Embodiments C1-C4, further comprising: one or more urging elements configured to keep the first section and the second section close to each other.

Embodiment C6. The jamming device of Embodiment C5, wherein the one or more urging elements comprise at least one of a highly compliant outer layer, a highly compliant inner layer, a fixed clearance limiting element, and a spring element.

Embodiment C7. The jamming device of any one of Embodiments C1-C6, wherein the sheet is packaged in a roll.

Embodiment C8. The jamming device of any one of Embodiments C1-C7, wherein the sheet comprises a line of weakness between adjacent sections.

Embodiment C9. The jamming device of any one of Embodiments C1-C8, wherein a coefficient of friction of the sheet is less than 0.4.

Embodiment C10. The jamming device of any one of Embodiments C1-C9, wherein a dielectric layer of the first section covers less than one hundred percent of a circumference of the first section.

Embodiment C11. The jamming device of any one of Embodiments C1-C10, wherein the dielectric layer has a thickness less than or equal to 5 micrometers.

Embodiment C12. The jamming device of any one of Embodiments C1-C11, wherein a direct path between the first conductive layer and the second conductive layer for at least one part of the jamming device is approximately the same length as the distance between the first and second conductive layers in the second state.

Embodiment C13. The jamming device of any one of Embodiments C1-C12, wherein the first sheet is separated from a large sheet having a conductive layer.

Embodiment C14. The jamming device of Embodiment C13, wherein the large sheet is a roll of sheet.

Embodiment C15. The jamming device of any one of Embodiments C1-C14, wherein the first sheet is patterned such that it is extensible in at least one axis.

Embodiment C16. The jamming device of any one of Embodiments C1-C15, wherein the first section has patterned openings such that it is extensible in at least one axis.

Embodiment C17. The jamming device of any one of Embodiments C1-C16, wherein the first section has a plurality of protruded features.

Embodiment C18. The jamming device of Embodiment C17, wherein the second section has a plurality of protruded features.

Embodiment C19. The jamming device of Embodiment C18, wherein at least some of the plurality of protruded features of the first section are mated with some of the plurality of protruded features of the second section in the second state.

Embodiment C20. The jamming device of any one of Embodiments C1-C19, wherein the dielectric layer has a relative permittivity greater than 3.

Embodiment C21. The jamming device of any one of Embodiments C1-C20, wherein the dielectric layer comprises an inorganic compound.

Embodiment C22. The jamming device of any one of Embodiments C1-C21, wherein the sheet comprises a core layer providing structural support.

Embodiment C23. The jamming device of any one of Embodiments C1-C22, wherein the dielectric layer has a thickness less than or equal to 10 micrometers.

Embodiment C24. The jamming device of any one of Embodiments C1-C23, wherein the dielectric layer is a coating on the sheet.

Embodiment D1. A method including the steps of: retrieving a sheet having a conductive layer and a dielectric layer; separating a first set of sections from the sheet; connecting the first set of sections electrically via a first connector; separating a second set of sections from the sheet; connecting the second set of sections electrically via a second connector; and assembling the first set of sections and the second set of sections into a jamming device. The sheet is non-extensible and flexible. The first set of sections and the second set of sections are slidable relative to each adjacent pair in a first state. The first set of sections and the second set of sections are jammed together in a second state when a voltage is applied between the first connector and the second connector.

Embodiment D2. The method of Embodiment D1, wherein the dielectric layer is a coating on the sheet.

Embodiment D3. The method of Embodiment D1 or D2, wherein the dielectric layer has a thickness less than or equal to 10 micrometers.

Embodiment D4. The method of any one of Embodiments D1-D3, wherein the dielectric layer has a thickness less than or equal to 5 micrometers.

Embodiment D5. The method of any one of Embodiments D1-D4, further comprising: assembling the first set of sections and the second set of sections with one or more urging elements.

Embodiment D6. The method of Embodiment D5, wherein the one or more urging elements comprise at least one of a highly compliant outer layer, a highly compliant inner layer, a fixed clearance limiting element, and a spring element.

Embodiment D7. The method of any one of Embodiments D1-D6, wherein the sheet is packaged in a roll.

Embodiment D8. The method of any one of Embodiments D1-D7, wherein the sheet comprises a line of weakness between adjacent sections.

Embodiment D9. The method of any one of Embodiments D1-D8, wherein a coefficient of friction of the sheet is less than 0.4.

Embodiment D10. The method of any one of Embodiments D1-D9, wherein the dielectric layer of at least one of the first set of sections covers less than one hundred percent of a circumference of the at least one of the first set of sections.

Embodiment D11. The method of any one of Embodiments D1-D10, wherein a distance between an adjacent one of the first set of sections and one of the second set of sections is no greater than 10 micrometers in the first state.

Embodiment D12. The method of any one of Embodiments D1-D11, wherein a direct path between two conductive layers of the adjacent one of the first set of sections and one of the second set of sections is approximately the same length as the distance between the two conductive layers in the second state.

Embodiment D13. The method of any one of Embodiments D1-D12, wherein the sheet is patterned such that it is extensible along at least one axis.

Embodiment D14. The method of any one of Embodiments D1-D13, wherein the sheet has patterned openings such that it is extensible along at least one axis.

Embodiment D15. The method of any one of Embodiments D1-D14, wherein the sheet has a plurality of protruded features.

Embodiment D16. The method of Embodiment D15, wherein at least some of the plurality of protruded features of at least one of the first set of sections are mated with some of the plurality of protruded features of at least one of the second set of sections in the second state.

Embodiment D17. The method of any one of Embodiments D1-D16, wherein the dielectric layer has a relative permittivity greater than 3.

Embodiment D18. The method of any one of Embodiments D1-D17, wherein the dielectric layer comprises an inorganic compound.

Embodiment D19. The method of any one of Embodiments D1-D18, wherein the sheet comprises a core layer providing structural support.

Embodiment D20. The method of any one of Embodiments D1-D19, wherein the applied voltage is less than or equal to a break-down voltage of air at a distance between the first and the second conductive layer.

Embodiment D21. The method of any one of Embodiments D1-D20, wherein the applied voltage is no greater than 100V.

Embodiment E1. An electrostatic sheet jamming apparatus comprising a first sheet comprising a first conductive layer, the first sheet comprising a set of first features protruded from a first general plane of the first sheet, a first dielectric layer disposed adjacent to the first conductive layer, and a second sheet comprising a second conductive layer and disposed proximate to the first dielectric layer, the second sheet comprising a set of second features protruded from a second general plane of the second sheet. The first dielectric layer is disposed between the first conductive layer and the second conductive layer. The first sheet and the second sheet are non-extensible and flexible, wherein at least some of the set of first features are configured to mate with at least some of the set of second features. The first sheet and the second sheet are movable relative each other in a first state. The first sheet and the second sheet are jammed with each other in a second state when a voltage is applied between the first conductive layer and the second conductive layer.

Embodiment E2. The apparatus of Embodiment E1, wherein the set of first features has a first height representing an average height of the set of first features from the first general plane.

Embodiment E3. The apparatus of Embodiment E2, wherein the first height is equal to or less than 10 millimeters.

Embodiment E4. The apparatus of Embodiment E2, wherein the first height is equal to or less than 1 millimeters.

Embodiment E5. The apparatus of Embodiment E2, wherein the set of second features has a second height representing an average height of the set of second features from the second general plane.

Embodiment E6. The apparatus of Embodiment E5, wherein the second height is equal to or less than 10 millimeters.

Embodiment E7. The apparatus of Embodiment E5, wherein the second height is equal to or less than 1 millimeters.

Embodiment E8. The apparatus of any one of Embodiments E1-E7, wherein one of the set of first features is a prism, a pyramid, a rectangular protrusion, an ellipsoidal protrusion, a sawtooth, or a sinusoid.

Embodiment E9. The apparatus of any one of Embodiments E1-E8, wherein the first conductive layer is a coating on the first sheet.

Embodiment E10. The apparatus of any one of Embodiments E1-E9, wherein the first dielectric layer is a coating on the first sheet.

Embodiment E11. The apparatus of Embodiment E10, further comprising: a second dielectric layer coated on the second sheet.

Embodiment E12. The apparatus of Embodiment E11, wherein the second dielectric layer has a thickness less than or equal to 5 micrometers.

Embodiment E13. The apparatus of any one of Embodiments E1-E12, wherein at least some of the set of first features have a same first shape.

Embodiment E14. The apparatus of Embodiment E13, wherein at least some of the set of first features have a same second shape.

Embodiment E15. The apparatus of Embodiment E14, wherein the first shape is a same shape as the second shape.

Embodiment E16. The apparatus of any one of Embodiments E1-E15, wherein some of the set of first features are mated with some of the set of second features in the second state.

Embodiment E17. The apparatus of Embodiment E16, wherein the some of the set of first features are in contact with the some of the set of second features.

Embodiment E18. The apparatus of any one of Embodiments E1-E17, wherein the applied voltage is no greater than a break-down voltage of a distance between the first and the second conductive layer.

Embodiment E19. The apparatus of any one of Embodiments E1-E18, wherein the applied voltage is no greater than 100V.

Embodiment E20. The apparatus of any one of Embodiments E1-E19, further comprising: one or more urging elements configured to keep the first sheet and the second sheet close to each other.

Embodiment E21. The apparatus of Embodiment E20, wherein the one or more urging elements comprise at least one of a highly compliant outer layer, a highly compliant inner layer, a fixed clearance limiting element, and a spring element.

Embodiment E22. The apparatus of any one of Embodiments E1-E21, wherein the first dielectric layer has a thickness less than or equal to 10 micrometers.

Embodiment E23. The apparatus of any one of Embodiments E1-E22, wherein the first dielectric layer has a thickness less than or equal to 5 micrometers.

Embodiment E24. The apparatus of any one of Embodiments E1-E23, wherein the first sheet is separated from a large sheet having a conductive layer.

Embodiment E25. The apparatus of Embodiment E24, wherein the large sheet is a roll of sheet.

Embodiment E26. The apparatus of any one of Embodiments E1-E25, wherein the first sheet is patterned such that it is extensible in at least one axis.

Embodiment E27. The apparatus of any one of Embodiments E1-E26, wherein the first dielectric layer has a relative permittivity greater than 3.

Embodiment E28. The apparatus of any one of Embodiments E1-E27, wherein the first dielectric layer comprises an inorganic compound.

Embodiment E29. The apparatus of any one of Embodiments E1-E28, wherein at least one of the first sheet and the second sheet comprises a core layer providing structural support.

Embodiment F1. An electrostatic sheet jamming apparatus comprising: a first set of sheets, each of the first set of sheets comprising a first conductive layer, a second set of sheets, each of the second set of sheets comprising a second conductive layer, a first connector electrically conductively connected to the first conductive layers of at least part of the first set of sheets, a second connector electrically conductively connected to the second conductive layers of at least part of the second set of sheets, and a set of dielectric layers. The first set of sheets are connected on two edges. The second set of sheets are connected on two edges. The first set of sheets and the second set of sheets are interdigitated, wherein each of the adjacent pair of the first set of sheets and the second set of sheets has one of the set of dielectric layers disposed in between. The first set of sheets and the second set of sheets are movable relative to each other in a first state. The first set of sheets and the second set of sheets are jammed with each other in a second state when a voltage is applied between the first connector and the second connector.

Embodiment F2. The apparatus of Embodiment F1, wherein at least some of dielectric layers are coated on the first set of sheets.

Embodiment F3. The apparatus of Embodiment F2, wherein at least some of dielectric layers are coated on the second set of sheets.

Embodiment F4. The apparatus of any one of Embodiments F1-F3, wherein the first set of sheets and the second set of sheets are interdigitated with an angle greater than 0 degree.

Embodiment F5. The apparatus of any one of Embodiments F1-F4, wherein the first set of sheets are connected on two opposing edges.

Embodiment F6. The apparatus of any one of Embodiments F1-F5, wherein the first set of sheets are connected on two adjacent edges.

Embodiment F7. The apparatus of Embodiment F6, wherein the second set of sheets are connected on two adjacent edges.

Embodiment F8. The apparatus of Embodiment F7, wherein the first set of sheets are rotatable relative to the second set of sheets in the first state.

Embodiment F9. The apparatus of any one of Embodiments F1-F8, further comprising: one or more urging elements configured to keep the first set of sheets and the second set of sheets close to each other.

Embodiment F10. The apparatus of Embodiment F9, wherein the one or more urging elements comprise at least one of a highly compliant outer layer, a highly compliant inner layer, a fixed clearance limiting element, and a spring element.

Embodiment F11. The apparatus of any one of Embodiments F1-F10, wherein a distance between an adjacent pair of the first conductive layer and the second conductive layer in the first state is no greater than 10 micrometers.

Embodiment F12. The apparatus of any one of Embodiments F1-F11, wherein a distance between an adjacent pair of the first conductive layer and the second conductive layer in the first state is no greater than 5 micrometers.

Embodiment F13. The apparatus of any one of Embodiments F1-F12, wherein at least one of the set of dielectric layers has a thickness less than or equal to 10 micrometers.

Embodiment F14. The apparatus of any one of Embodiments F1-F13, wherein at least one of the set of dielectric layers has a thickness less than or equal to 5 micrometers.

Embodiment F15. The apparatus of any one of Embodiments F1-F14, wherein the applied voltage is no greater than 100V.

Embodiment F16. The apparatus of Embodiment F15, wherein the applied voltage is less than or equal to a break-down voltage of air at a distance between adjacent one of the first set of sheets and one of the second set of sheets.

Embodiment F17. The apparatus of any one of Embodiments F1-F16, wherein the first set of sheets are separated from a large sheet having a conductive layer.

Embodiment F18. The apparatus of Embodiment F17, wherein the large sheet is a roll of sheet.

Embodiment F19. The apparatus of any one of Embodiments F1-F18, wherein at least one of the first set of sheets is patterned such that it is extensible in at least one axis.

Embodiment F20. The apparatus of any one of Embodiments F1-F19, wherein at least one of the first set of sheets has patterned openings such that it is extensible in at least one axis.

Embodiment F21. The apparatus of any one of Embodiments F1-F20, wherein at least one of the first set of sheets has a plurality of protruded features.

Embodiment F22. The apparatus of Embodiment F21, wherein at least one of the first set of sheets has a plurality of protruded features.

Embodiment F23. The apparatus of Embodiment F22, wherein at least some of the plurality of protruded features of at least one of the first set of sheets are mated with some of the plurality of protruded features of at least one of the second set of sheets in the second state.

Embodiment F24. The apparatus of any one of Embodiments F1-F23, wherein at least one of the set of dielectric layers has a relative permittivity greater than 3.

Embodiment F25. The apparatus of any one of Embodiments F1-F24, wherein at least one of the set of dielectric layers comprises an inorganic compound.

Embodiment F26. The apparatus of any one of Embodiments F1-F25, wherein a coefficient of friction of at least one of the first set of sheets is less than 0.4.

Embodiment F27. The apparatus of any one of Embodiments F1-F26, wherein at least one of the first set of sheets comprises a core layer providing structural support.

Embodiment G1. An electrostatic sheet jamming apparatus comprising a first sheet comprising a first conductive layer, a first dielectric layer disposed adjacent to the first conductive layer, a second sheet comprising a second conductive layer and disposed proximate to the first dielectric layer. The first dielectric layer is disposed between the first conductive layer and the second conductive layer. The first sheet and the second sheet are made of non-extensible materials and flexible. The first sheet comprises a set of first slit features such that the first sheet is extensible on a first axis. The second sheet comprises a set of second slit features such that the second sheet is extensible on a second axis. The first sheet and the second sheet are slidable relative to each other in a first state. The first sheet and the second sheet are locked against each other in a second state when a voltage is applied between the first conductive layer and the second conductive layer.

Embodiment G2. The apparatus of Embodiment G1, wherein the first conductive layer is a coating on the first sheet.

Embodiment G3. The apparatus of Embodiment G1 or G2, wherein the first dielectric layer is a coating on the first sheet.

Embodiment G4. The apparatus of any one of Embodiments G1-G3, wherein one of the set of first slit features is an elongated opening, a triangle opening, and an oval opening.

Embodiment G5. The apparatus of any one of Embodiments G1-G4, wherein at least one of the first and second sheets are extensible in one axis.

Embodiment G6. The apparatus of any one of Embodiments G1-G5, wherein at least one of the first and second sheets are extensible in more than one axis.

Embodiment G7. The apparatus of any one of Embodiments G1-G6, further comprising: one or more urging elements configured to keep the first sheet and the second sheet close to each other.

Embodiment G8. The apparatus of Embodiment G7, wherein each of the one or more urging elements comprises a highly compliant outer layer.

Embodiment G9. The apparatus of Embodiment G7, wherein each of the one or more urging elements comprises a highly compliant inner layer.

Embodiment G10. The apparatus of Embodiment G7, wherein at least one of the one or more urging elements is made of a stretchable material.

Embodiment G11. The apparatus of any one of Embodiments G1-G10, wherein the second axis is parallel to the first axis.

Embodiment G12. The apparatus of any one of Embodiments G1-G11, further comprising: a second dielectric layer coated on the second sheet.

Embodiment G13. The apparatus of any one of Embodiments G1-G12, wherein the applied voltage is no greater than a break-down voltage of a distance between the first and the second conductive layer.

Embodiment G14. The apparatus of any one of Embodiments G1-G13, wherein the applied voltage is no greater than 100V.

Embodiment G15. The apparatus of any one of Embodiments G1-G14, wherein the first dielectric layer has a thickness less than or equal to 10 micrometers.

Embodiment G16. The apparatus of any one of Embodiments G1-G15, wherein the first dielectric layer has a thickness less than or equal to 5 micrometers.

Embodiment G17. The apparatus of any one of Embodiments G1-G16, wherein the first sheet is separated from a large sheet having a conductive layer.

Embodiment G18. The apparatus of Embodiment G17, wherein the large sheet is a roll of sheet.

Embodiment G19. The apparatus of any one of Embodiments G1-G18, wherein the first sheet is patterned such that it is extensible in at least one axis.

Embodiment G20. The apparatus of any one of Embodiments G1-G19, wherein the first dielectric layer has a relative permittivity greater than 3.

Embodiment G21. The apparatus of any one of Embodiments G1-G20, wherein the first dielectric layer comprises an inorganic compound.

Embodiment G22. The apparatus of any one of Embodiments G1-G21, wherein at least one of the first sheet and the second sheet comprises a core layer providing structural support.

Embodiment H1. A flexible electronic device, comprising: a flexible component layer comprising at least one electronic component, and a jamming device disposed proximate to the flexible component layer. The jamming device permits the flexible component layer to be bent in a first state. The jamming device is configured to resist bending of the flexible component layer in a second state.

Embodiment H2. The electronic device of Embodiment H1, wherein the jamming device comprises a plurality of sheets.

Embodiment H3. The electronic device of Embodiment H2, wherein the plurality of sheets comprises conductive layers such that the jamming device are jammable electrostatically.

Embodiment H4. The electronic device of Embodiment H2, wherein the jamming device are jammable by a vacuum.

Embodiment H5. The electronic device of Embodiment H2, wherein at least some of the plurality of sheets are substantially conform to a primary surface of the flexible component layer.

Embodiment H6. The electronic device of Embodiment H2, wherein at least some of the plurality of sheets are substantially perpendicular to a primary surface of the flexible component layer.

Embodiment H7. The electronic device of any one of Embodiments H1-H6, wherein the electronic device is a display.

Embodiment H8. The electronic device of any one of Embodiments H1-H7, wherein the electronic device is a wearable electronic device.

Embodiment H9. The electronic device of Embodiment H3, wherein the plurality of sheets comprises a first set of sheets and a second set of sheets, wherein the first set of sheets and the second set of sheets are interdigitated, and wherein the second state is induced when a voltage is applied between the first set of sheets and the second set of sheets.

Embodiment H10. The electronic device of Embodiment H9, further comprising a set of dielectric layers.

Embodiment H11. The electronic device of Embodiment H10, wherein at least some of the set of dielectric layers are coated on the first set of sheets.

Embodiment H12. The electronic device of Embodiment H11, wherein at least some of the set of dielectric layers are coated on the second set of sheets.

Embodiment H13. The electronic device of any one of Embodiments H9-H12, wherein a distance between an adjacent pair of the first conductive layer and the second conductive layer in the first state is no greater than 10 micrometers.

Embodiment H14. The electronic device of any one of Embodiments H9-H13, wherein the first dielectric layer covers less than one hundred percent of a circumference of the first sheet.

Embodiment H15. The electronic device of any one of Embodiments H9-H14, wherein the applied voltage is less than or equal to a break-down voltage of air at a distance between adjacent one of the first set of sheets and one of the second set of sheets.

Embodiment H16. The electronic device of any one of Embodiments H9-H15, wherein the applied voltage is no greater than 100V.

Embodiment H17. The electronic device of any one of Embodiments H9-H16, further comprising: one or more urging elements configured to keep the first set of sheets and the second set of sheets close to each other.

Embodiment H18. The electronic device of Embodiment H17, wherein the one or more urging elements comprise at least one of a highly compliant outer layer, a highly compliant inner layer, a fixed clearance limiting element, and a spring element.

Embodiment H19. The electronic device of any one of Embodiments H9-H18, wherein at least one of the set of dielectric layers has a thickness less than or equal to 10 micrometers.

Embodiment H20. The electronic device of any one of Embodiments H9-H19, wherein at least one of the set of dielectric layers has a thickness less than or equal to 5 micrometers.

Embodiment H21. The electronic device of any one of Embodiments H9-H20, wherein the first set of sheets are separated from a large sheet having a conductive layer.

Embodiment H22. The electronic device of Embodiment H21, wherein the large sheet is a roll of sheet.

Embodiment H23. The electronic device of any one of Embodiments H2-H22, wherein at least one of the set of sheets is patterned such that the at least one of the set of sheets is extensible in at least one axis.

Embodiment H24. The electronic device of any one of Embodiments H2-H23, wherein at least one of the first set of sheets has patterned openings such that it is extensible in at least one axis.

Embodiment H25. The electronic device of any one of Embodiments H9-H24, wherein at least one of the first set of sheets has a plurality of protruded features.

Embodiment H26. The electronic device of Embodiment H25, wherein at least one of the second set of sheets has a plurality of protruded features.

Embodiment H27. The electronic device of Embodiment H26, wherein at least some of the plurality of protruded features of at least one of the first set of sheets are mated with some of the plurality of protruded features of at least one of the second set of sheets in the second state.

Embodiment H28. The electronic device of Embodiment H10, wherein at least one of the set of dielectric layers has a relative permittivity greater than 3.

Embodiment H29. The electronic device of Embodiment H10, wherein at least one of the set of dielectric layers comprises an inorganic compound.

Embodiment H30. The electronic device of any one of Embodiments H2-H29, wherein a coefficient of friction of at least one of the set of sheets is less than 0.4.

Embodiment H31. The electronic device of any one of Embodiments H2-H30, wherein at least one of the set of sheets comprises a core layer providing structural support.

EXAMPLES

Example 1

A roll of polyethylene terephthalate (PET) that was 0.002 inch (0.00508 cm) thick was sputter coated with a 0.030 micrometer thick layer of copper on one side as a conductive layer, and then reactively sputter coated with a 0.050 micrometer thick layer of silicon aluminum oxide as a dielectric layer over the copper layer. Eighteen sheets were cut from the roll into strips that were 6 inches (15.24 cm) wide by 15 inches (18.1 cm) long. The strips were combined into double sided electrostatic jamming sheets by placing sets of two sheets with the plain PET surfaces touching.

Figure 8:
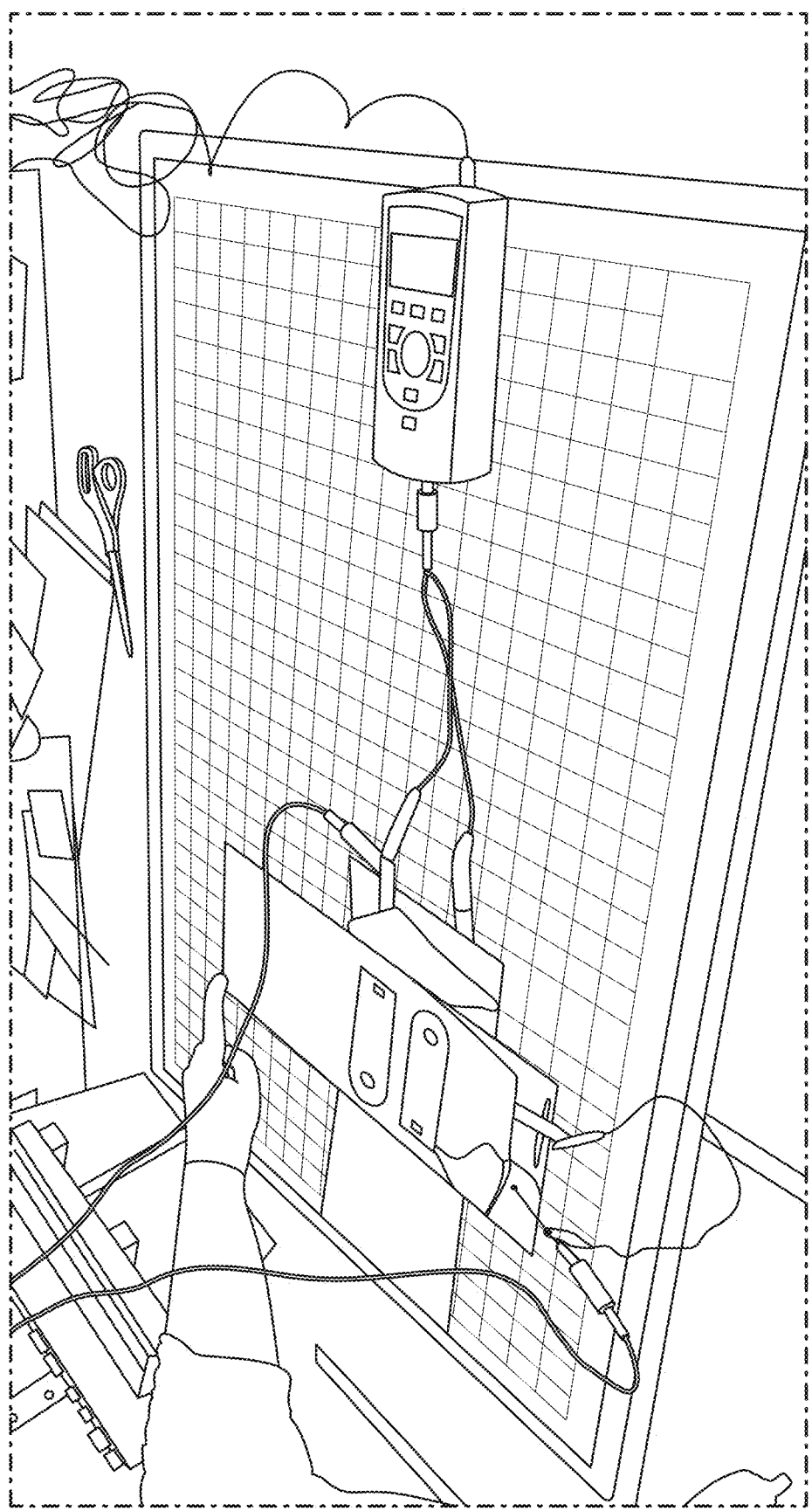
FIG. 8 illustrates a lab prototype of a jamming device.

The double sided electrostatic jamming sheets were then assembled into two sets of interdigitated sheets as shown in FIG. 1F. The two sets of sheets were electrically and mechanically connected together with conductive tape as shown in FIG. 1F. The strips were laid on a table with the long axis of one set perpendicular to the other set as shown in FIG. 8. One of the sets was then secured to the table, and two aluminum weights (total mass of 17.95 g) were placed on the intersection of the sets to urge them into proximity without excessive pressure. Varying voltages were applied between the sets of jamming sheets while the one set was pulled slowly with a Chatillon DFS-050 digital force gauge (available at Ametek, Inc., Berwyn, PA, United States). The average force required to pull the set was recorded. Sets of 3 trials were made at a voltage level and 3 trials at zero voltage were made between each set of powered trials. The applied voltage and average resulting force for all the trials is summarized in Table 1.

TABLE 1

| Trial set # | Voltage (V) | Average Force (N) |
|---|---|---|
| 1 | 0 | 0.67 |
| 2 | 5 | 0.75 |
| 3 | 0 | 0.63 |
| 4 | 10 | 0.96 |
| 5 | 0 | 0.68 |
| 6 | 15 | 2.07 |
| 7 | 0 | 0.61 |
| 8 | 20 | 3.83 |
| 9 | 0 | 0.76 |

The results showed that a significant pressure can be achieved at very low voltage levels. The consistent return to a low force at zero voltage demonstrates that we have not created an electric field that is so strong that it polarizes the materials or injects space charge into the system. The results match the model as discussed above well. They fit the expected quadratic relationship with an $R^2$ value of 0.994. With an area A of 36 square inch (232.258 $cm^2$) and N=9 interfaces, we can estimate the coefficient of friction from the zero voltage data to be $\mu=0.044$. The jamming pressure caused by electrostatic jamming at 20V is estimated to be about 416 Pa.

The present invention should not be considered limited to the particular examples and embodiments described above, as such embodiments are described in detail to facilitate explanation of various aspects of the invention. Rather the present invention should be understood to cover all aspects of the invention, including various modifications, equivalent processes, and alternative devices falling within the spirit and scope of the invention as defined by the appended claims and their equivalents.

What is claimed is:

1. An electrostatic sheet jamming device comprising:
   a first set of sheets, each sheet comprising two dielectric layers and two first conductive layers disposed between the two dielectric layers, with a core layer being disposed between the two first conductive layers, wherein at least one sheet of the first set of sheets includes a core layer;
   a second set of sheets, each sheet comprising a second conductive layer;
   a set of dielectric layers; and
   a first connector electrically conductively connected to first conductive layers of at least part of the first set of sheets;
   a second connector electrically conductively connected to second conductive layers of at least part of the second set of sheets;
   wherein the first set of sheets and the second set of sheets are interdigitated,
   wherein each of the adjacent pair of the first set of sheets and the second set of sheets has one of the set of dielectric layers disposed in between,
   wherein each of the set of dielectric layers has a thickness less than or equal to 10 micrometers,
   wherein the first set of sheets and the second set of sheets are slidable relative to each other in a first state,
   wherein the first set of sheets and the second set of sheets are jammed with each other in a second state when a voltage is applied between the first connector and the second connector, and wherein the applied voltage is less than or equal to a break-down voltage of air at a distance between adjacent conductive layers of one of the first set of sheets and one of the second set of sheets.

2. The electrostatic sheet jamming device of claim 1, wherein a distance between an adjacent pair of the first conductive layer and the second conductive layer in the first state is no greater than 10 micrometers.

3. The electrostatic sheet jamming device of claim 1, wherein the applied voltage is less than 100V.

4. The electrostatic sheet jamming device of claim 1, wherein at least one of the first set of sheets is patterned such that it is extensible in at least one axis.

5. The electrostatic sheet jamming device of claim 1, wherein at least one of the first set of sheets has a plurality of protruded features.

6. An electrostatic sheet jamming device comprising:
a first set of sheets, each sheet of the first set of sheets comprising two first dielectric layers, two first conductive layers are disposed between the two first dielectric layers, and a core layer is disposed between the two first conductive layers, wherein at least one sheet of the first set of sheets includes a core layer;
a second set of sheets, each sheet of the second set of sheets comprising two second dielectric layers, two second conductive layers disposed between the two second dielectric layers, and a core layer disposed between the two second conductive layers;
a set of dielectric layers;
a first connector electrically conductively connected to first conductive layers of at least part of the first set of sheets; and
a second connector electrically conductively connected to second conductive layers of at least part of the second set of sheets;
wherein the first set of sheets and the second set of sheets are interdigitated,
wherein each of the adjacent pair of the first set of sheets and the second set of sheets has one of the set of dielectric layers disposed in between,
wherein each of the set of dielectric layers has a thickness less than or equal to 10 micrometers,
wherein the first set of sheets and the second set of sheets are slidable relative to each other in a first state,
wherein the first set of sheets and the second set of sheets are jammed with each other in a second state when a voltage is applied between the first connector and the second connector, and
wherein the applied voltage is less than or equal to a break-down voltage of air at a distance between adjacent conductive layers of one of the first set of sheets and one of the second set of sheets.

7. The electrostatic sheet jamming device of claim 6, wherein a distance between an adjacent pair of the first conductive layer and the second conductive layer in the first state is no greater than 10 micrometers.

8. The electrostatic sheet jamming device of claim 6, wherein the applied voltage is less than 100V.

9. The electrostatic sheet jamming device of claim 6, wherein at least one of the first set of sheets is patterned such that it is extensible in at least one axis.

10. The electrostatic sheet jamming device of claim 6, wherein at least one of the first set of sheets has a plurality of protruded features.

11. An electrostatic sheet jamming device comprising:
a first set of sheets, each sheet of the first set of sheets comprising a first core layer and a first dielectric layer;
a second set of sheets, each seet of the second set of sheets comprising two second dielectric layers, two second conductive layers disposed between the two second dielectric layers, and a second core layer disposed between the two second conductive layers, wherein each respective second conductive layer being adjacent to a respective second core layer and a respective second dielectric layer in each sheet of the second set of sheets;
a set of dielectric layers;
a first connector electrically conductively connected to first conductive layers of at least part of the first set of sheets; and
a second connector electrically conductively connected to second conductive layers of at least part of the second set of sheets,
wherein the first set of sheets and the second set of sheets are interdigitated,
wherein each of the adjacent pair of the first set of sheets and the second set of sheets has one of the set of dielectric layers disposed in between,
wherein each of the set of dielectric layers has a thickness less than or equal to 10 micrometers,
wherein the first set of sheets and the second set of sheets are slidable relative to each other in a first state,
wherein the first set of sheets and the second set of sheets are jammed with each other in a second state when a voltage is applied between the first connector and the second connector, and
wherein the applied voltage is less than or equal to a break-down voltage of air at a distance between adjacent conductive layers of one of the first set of sheets and one of the second set of sheets.

12. The electrostatic sheet jamming device of claim 11, wherein a distance between an adjacent pair of the first conductive layer and the second conductive layer in the first state is no greater than 10 micrometers.

13. The electrostatic sheet jamming device of claim 11, wherein the applied voltage is less than 100V.

14. The electrostatic sheet jamming device of claim 11, wherein at least one of the first set of sheets is patterned such that it is extensible in at least one axis.

15. The electrostatic sheet jamming device of claim 11, wherein at least one of the first set of sheets has a plurality of protruded features.

* * * * *

UNITED STATES PATENT AND TRADEMARK OFFICE
CERTIFICATE OF CORRECTION

| | | |
|---|---|---|
| PATENT NO. | : 12,132,419 B2 | Page 1 of 1 |
| APPLICATION NO. | : 17/932471 | |
| DATED | : October 29, 2024 | |
| INVENTOR(S) | : Thomas Richard Johnstone Corrigan | |

It is certified that error appears in the above-identified patent and that said Letters Patent is hereby corrected as shown below:

In the Claims

Column 30
Line 12, in Claim 11, delete "each seet" and insert -- each sheet --, therefor.

Signed and Sealed this
Tenth Day of June, 2025

Coke Morgan Stewart
*Acting Director of the United States Patent and Trademark Office*